(12) United States Patent
Shtein et al.

(10) Patent No.: US 12,208,227 B2
(45) Date of Patent: Jan. 28, 2025

(54) PRECISION BIO-CHEMOTRONIC SYSTEM

(71) Applicant: THE REGENTS OF THE UNIVERSITY OF MICHIGAN, Ann Arbor, MI (US)

(72) Inventors: Max Shtein, Ann Arbor, MI (US); Olga Shalev, Nazareth-Illit (IL); Y. Eugene Shteyn, Cupertino, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 820 days.

(21) Appl. No.: 16/641,505

(22) PCT Filed: Aug. 24, 2018

(86) PCT No.: PCT/US2018/047994
§ 371 (c)(1),
(2) Date: Feb. 24, 2020

(87) PCT Pub. No.: WO2019/040898
PCT Pub. Date: Feb. 28, 2019

(65) Prior Publication Data
US 2021/0145335 A1 May 20, 2021

Related U.S. Application Data

(60) Provisional application No. 62/549,786, filed on Aug. 24, 2017.

(51) Int. Cl.
*A61M 37/00* (2006.01)
*A61B 5/00* (2006.01)
(Continued)

(52) U.S. Cl.
CPC ......... *A61M 37/00* (2013.01); *A61B 5/14735* (2013.01); *A61B 5/411* (2013.01);
(Continued)

(58) Field of Classification Search
CPC .. A61K 9/0009; A61K 9/2007; A61K 9/7023; A61K 9/703; A61K 9/7084;
(Continued)

(56) References Cited

U.S. PATENT DOCUMENTS 5,474,796 A 12/1995 Brennan
5,605,662 A 2/1997 Heller et al.
(Continued)

FOREIGN PATENT DOCUMENTS

CN 106904002 A 6/2017
WO 84/03564 A1 9/1984
(Continued)

OTHER PUBLICATIONS

Baghel. S. et al., "Polymeric Amorphous Solid Dispersions: A Review of Amorphization, Crystallization, Stabilization, Solid-State Characterization, and Aqueous Solubilization of Biopharmaceutical Classification System Class II Drugs," Journal of Pharmaceutical Sciences in press, 1-18 (2016).
(Continued)

*Primary Examiner* — Kami A Bosworth
(74) *Attorney, Agent, or Firm* — MARSHALL, GERSTEIN & BORUN LLP

(57) ABSTRACT

A solid film structure formed of multiple solid film insert layers each having different functionality is provided. The solid film structure forms a bio-chemotronic structure having an actuator thin film layer with one or more low molecular weight organic active agents that may be activated, a sensor thin film layer that includes one or more sensors for measuring a direct or indirect response from a target to the one or more active agents, and a control thin film layer configured to individually control activation of the active agents in the actuator layer, e.g., according to a protocol.

24 Claims, 33 Drawing Sheets

(51) Int. Cl.
*A61B 5/1473* (2006.01)
*A61K 9/00* (2006.01)
*A61K 9/70* (2006.01)
*G16H 40/63* (2018.01)

(52) U.S. Cl.
CPC .......... *A61K 9/0009* (2013.01); *A61K 9/7007* (2013.01); *A61M 37/0069* (2013.01); *A61B 2562/164* (2013.01); *A61M 37/0015* (2013.01); *A61M 2205/3303* (2013.01); *A61M 2205/3576* (2013.01); *A61M 2230/005* (2013.01); *G16H 40/63* (2018.01)

(58) Field of Classification Search
CPC ... A61K 9/7092; A61B 5/14735; A61B 5/411; A61B 2562/164; A61M 37/00; A61M 2202/0067; A61M 2202/0078; A61M 2205/0244; A61M 2205/04; A61M 2205/3303; A61M 2230/005
See application file for complete search history.

(56) References Cited

U.S. PATENT DOCUMENTS

| | | | |
|---|---|---|---|
| 2002/0099359 A1* | 7/2002 | Santini, Jr. | A61K 9/0009 604/521 |
| 2004/0087916 A1 | 5/2004 | Pickup et al. | |
| 2005/0096587 A1* | 5/2005 | Santini, Jr. | A61B 5/1486 604/110 |
| 2005/0267440 A1* | 12/2005 | Herman | A61B 5/14528 604/20 |
| 2006/0057737 A1* | 3/2006 | Santini, Jr. | A61K 9/0097 604/890.1 |
| 2008/0044314 A1 | 2/2008 | McIntyre et al. | |
| 2008/0076975 A1* | 3/2008 | Santini, Jr. | A61K 47/12 600/300 |
| 2008/0109252 A1 | 5/2008 | Lafountain et al. | |
| 2009/0018413 A1 | 1/2009 | Santini, Jr. et al. | |
| 2010/0021620 A1 | 1/2010 | Coates et al. | |
| 2010/0062529 A1 | 3/2010 | Zimmermann et al. | |
| 2014/0296996 A1 | 10/2014 | Shim et al. | |
| 2015/0250926 A1 | 9/2015 | McClain et al. | |
| 2016/0055316 A1 | 2/2016 | Jafari et al. | |
| 2016/0298947 A1 | 10/2016 | Rubin | |
| 2017/0035968 A1* | 2/2017 | Hassan | A61M 5/1723 |
| 2017/0262604 A1 | 9/2017 | Francois | |
| 2018/0296494 A1 | 10/2018 | Shalev et al. | |

FOREIGN PATENT DOCUMENTS

| | | |
|---|---|---|
| WO | 95/25116 A1 | 9/1995 |
| WO | 95/35505 A1 | 12/1995 |
| WO | 2011/035177 A2 | 3/2011 |

OTHER PUBLICATIONS

Beyer. et al., "The prediction, morphology, and mechanical properties of the polymorphs of paracetamol," Journal of the American Chemical Society 123: 5086-5094 (2001).
Biswas. et al., "Solvent-free, direct printing of organic semiconductors in atmosphere," Appl. Phys. Lett. 96: 263301-1-3 (2010).
Biswas. et al., "Spatial Mapping of Morphology and Electronic Properties of Air-Printed Pentacene Thin Films," Adv. Funct. Mater. 24, 3907-3916 (2014).
Biswas. et al., "Thin-Film Growth and Patterning Techniques for Small Molecular Organic Compounds Used in Optoelectronic Device Applications," Annu. Rev. Chem. Biomol. Eng., 4: 289-317 (2013).
Censi. et al., "Polymorph Impact on the Bioavailability and Stability of Poorly Soluble Drugs," Molecules 20: 18759-18776 (2015).
Derollez. et al., "Ab initio structure determination of the high-temperature phase of anhydrous caffeine by X-ray powder diffraction," Acta Cryst. 861: 329-334 (2005).

Enright. et al., "The Structure of Two Anhydrous Polymorphs of Caffeine from Single-Crystal Diffraction and Ultrahigh-Field Solid-State 13C NMR Spectroscopy," Crystal Growth & Design 7: 1406-1410 (2007).
Epple et al., "The phase transformation of caffeine: Investigation by dynamic X-ray diffraction and emanation thermal analysis," Thermochimica Acta, 250: 29-39 (1995).
European Application No. 18849133.6, Supplementary European Search Report and Opinion, mailed Apr. 21, 2021.
Han. et al., "Effect of pH on the structure and drug release profiles of layer-by-layer assembled films containing polyelectrolyte, micelles, and graphene oxide," Scientific reports 6: 24158, 1-10 (2016).
Heller. et al., "Discovery and analysis of inflammatory disease-related genes using cDNA microarrays," PNAS, 94(6): 2150-2155 (1997).
Hixsonz. et al., "Dependence of Reaction Velocity upon surface and Agitation," Industrial and engineering chemistry 23:10: 1160-1168 (1931).
International Application No. PCT/US2018/047994, International Preliminary Report on Patentability, mailed Mar. 5, 2020.
International Application No. PCT/US2018/047994, International Search Report and Written Opinion, mailed Oct. 17, 2018.
International Application No. PCT/US2020/028993, International Preliminary Report on Patentability, mailed Oct. 28, 2021.
International Application No. PCT/US2020/028993, International Search Report and Written Opinion, mailed Jul. 30, 2020.
International Application No. PCT/US2021/057299, International Search Report and Written Opinion, mailed Mar. 3, 2022.
International Application No. PCT/US2021/057299, Invitation to Pay Additional Fees, mailed Jan. 10, 2022.
Lehmann. et al., "The Crystal Structure of Anhydrous ß-Caffeine as Determined from X-ray Powder-Diffraction Data," Chemistry—A European Journal 13, 2908-2911 (2007).
Li. et al., "Steady State Morphologies of Paracetamol Crystal from Different Solvents," Crystal Growth & Design 17: 659-670 (2017).
Nelyubina. et al., "Higher density does not mean higher stability mystery of paracetamol finally unraveled," Chem. Commun. 46: 3469-3471 (2010).
Noyes. et al., "The Rate of Solution of Solid Substances in Their Own Solutions.," J. Am. Chem. Soc. 19: 930-934 (1897).
Precigoux. et al., "[p-(Dimethylamino-2 éthoxy) phényl]-1 trans-diphényl-1, 2 butène-1 (tamoxfène)(ICI-46474)," Acta Cryst. 835: 3070-3072 (1979).
Rodriguez-Hornedo. et al., "Significance of controlling crystallization mechanisms and kinetics in pharmaceutical systems," Journal of Pharmaceutical Sciences 88(7): 651-660 (1999).
Schena et al., "Parallel human genome analysis: microarray-based expression monitoring of 1000 genes.," PNAS, 93 (20): 10614-10619 (1996).
Shalev. et al., "Growth and modelling of spherical crystalline morphologies of molecular materials," Nature Communications, 5: 5204 (2014).
Shalev. O. et al., "Effect of crystal density on sublimation properties of molecular organic semiconductors," Organic Electronics, 14: 94-99 (2013).
Shtein et al, "Direct, Mask- and Solvent-Free Printing of Molecular Organic Semiconductors," ADV. mater, vol. 16, Issue 18, 2004, pp. 1615-1620.
Tseng. et al., "Determination of intrinsic dissolution rate using miniaturized rotating and stationary disk systems," Dissolution Technologies 21: 24-29 (2014).
Wang. et al., "Comparison and Analysis of Theoretical Models for Diffusion-Controlled Dissolution," Mol. Pharmaceutics 9: 1052-1066 (2012).
Warren. B.E, "X-Ray Diffraction," (Addison-Wesley Publishing Co., 1969).
Wu. Y. et al., "Polypyrrole based switchable filter system," conf proc IEEE eng med biol soc., 4090-4091 (2007).
Xu. et al., "Magnetic nanobelts of iron-doped zinc oxide," Appl. Phys. Lett. 86: 103 (2005).

* cited by examiner

PRECISION BIO-CHEMOTRONIC SYSTEM

CROSS-REFERENCE TO RELATED APPLICATIONS

This is a U.S. National Phase of International Application No. PCT/US2018/047994, filed Aug. 24, 2018, which The present application claims the benefit of U.S. Provisional Application No. 62/549,786, entitled "Precision Bio-Chemotronic System", filed on Aug. 24, 2017, which are hereby incorporated by reference herein in their entirety.

FIELD OF THE DISCLOSURE

The present disclosure generally relates to techniques for delivering active chemical agents to a subject and, more particularly, to techniques for electronically-controllable solid film devices formed of activatable chemical agents insert layers.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Data-driven precision healthcare, wellness, and biological system modification and testing have increased in interest with advancements in computer processing and in biologically-relevant data collection. Advancements in patient monitoring devices, systems, and methods have played a particularly important role in data collection. For example, various devices, systems, and methods are available for monitoring biologic activity, chemical reactions, or electronic processes within the body. Unfortunately, the accuracy of the monitoring is often limited by device, system, and/or method design, which affects where monitoring components are located on/in the body and the sensitivity of measurements, data relevance, processing capabilities, analysis techniques, etc. The result is that typical monitoring components, even in in vivo devices, may not result in accurate measurements and may not produce results relevant to successful treatment protocols. Further still, it is particularly difficult to detect side-effects from complex treatment procedures. Even where monitoring devices have been effective, they are typically limited to measuring only one type of bodily process (biologic activity, chemical activity, or electrical activity), and not multiple processes and multiple active agents. Moreover, the components and devices are typically complex designs that are not amenable to mass production, much less being amenable to adaptive, multiple purpose designs.

SUMMARY

The present application addresses the shortcomings of conventional devices, systems, and methods by providing bio-chemotronic insert components, devices, and systems for activating and/or monitoring processes on the surface or interior of a target. Examples of targets include but are not limited to: a subject (human, other animal), a natural or artificially created test tissue, a natural and/or artificial organ, a plant or a part(s) thereof, a distributed system (e.g. vascular system), a collection of cells (with or without reagent), organoid culture(s), and combinations thereof.

The bio-chemotronic insert components, devices, and systems herein are capable of following a stored and/or predetermined protocol, which may be adaptable to a desired application with regard to the at least one target. For example, a single bio-chemotronic insert component or device may be used to test numerous different biological activities, where the activities may vary based on the target, based on the location of interest, based on a desired treatment, etc.

The bio-chemotronic insert components, devices, and systems herein may be built upon a multiple-part bio-chemotronic insert design, where the bio-chemotronic insert includes at least one insert that serves as an actuator insert and at least one other insert that serves as a sensor insert. These inserts, which may each by fabricated using techniques such as organic vapor jet printing (OVJP), may be combined into a single insert that is integrated with an actuator and electronic controller layer configured to execute protocols to operate the bio-chemotronic insert. In some implementations, the integration of the electronic controller and actuator allows the inserts to be selectively operated and adapted to the particular application at hand. In other implementations, the controller and actuator may be distributed. For example, an insert may contain a frequency-responsive element that responds to inductive coupling of energy (e.g. radio-/microwave-frequency), or by light, or radiant heat, or sound waves.

Additionally, the activated protocol can be initiated by non-electronic means, for example using changes in pH, temperature, humidity, local atmospheric composition, pressure, shear, etc.

In yet other examples, non-electronic control mechanisms may be used, such as temperature controllers, humidity controllers, local atmospheric composition controllers, pressure controllers, shear controllers, pH sensors. For example, control may be implemented using a temperature-sensitive transformation or action, or humidity-sensitive/humidity-triggered transformation or action, etc. Further, control may involve the swelling of a polymer when wetted, or the dissolution of a membrane or separator upon a drop in pH, or a change in color when pH increases.

The electronic controllers of these bio-chemotronic inserts may communicate with an external processor such as a cloud based server, or other network-accessible controller capable of controlling operation of the bio-chemotronic insert. Indeed, the external controller is able to modify operation of the bio-chemotronic insert in response to sensed data from the target. This ability to control operation of a bio-chemotronic insert is particularly useful for bio-chemotronic inserts that have multiple operation capabilities. For example, bio-chemotronic inserts may have an actuator insert with multiple agents contained therein, each individually controllable for provision to the target. These actuator inserts have one or more activatable agents. The bio-chemotronic inserts may further have a sensor insert with multiple sensors for measuring different activities within the target.

In accordance with an example, an electronically-controllable solid film device, the device comprises: a solid film layer structure containing (i) an actuator insert having a low molecular weight organic active agent, wherein the low molecular weight organic active agent has a first state in the actuator insert in which the low molecular weight organic active agent is de-functionalized and a second state in which the low molecular weight organic active agent is functionalized for application to a target, and (ii) a sensor insert having a sensor configured to measure a response of the target to the applied low molecular weight organic active agent; an interface layer positioned for applying the electronically-controllable solid film device to the target; and a control layer positioned for communicating with the actuator insert and the sensor insert, the control layer configured to change the low molecular weight organic active agent from the first state to the second state and configured to receive response data from the sensor insert, the control layer comprising a processor.

In accordance with an example, a system comprises: an electronically-controllable solid film device, having, a solid film layer structure containing (i) an actuator insert having a low molecular weight organic active agent, wherein the low molecular weight organic active agent has a first state in the actuator insert in which the low molecular weight organic active agent is de-functionalized and a second state in which the low molecular weight organic active agent is functionalized for application to a target, and (ii) a sensor insert having a sensor configured to measure a response of the target to the applied low molecular weight organic active agent, and a control layer positioned for communicating with the actuator insert and the sensor insert, the control layer configured to change the low molecular weight organic active agent from the first state to the second state and configured to receive response data from the sensor insert, the control layer comprising a processor and a wireless transceiver; and a network-accessible controller having a processor and a memory, the network-accessible controller being configured to send a protocol instructions to the electronically-controllable solid film device, the protocol instructions including instructions on changing the low molecular weight organic active agent from the first state to the second state and instructions for operating the sensor in the sensor insert.

In accordance with an example, a solid film layer actuator insert comprises: a plurality of low molecular weight organic active agents, each having a first state in the actuator insert in which the low molecular weight organic active agent is de-functionalized and a second state in which the low molecular weight organic active agent is functionalized for application to a target, wherein each of the plurality of low molecular weight organic active agents are positioned in a different location in the actuator insert such that the first state is switchable to the second state for each of the plurality of low molecular weight organic active agents, without affecting the first state or second state of at least some of the other of the plurality of low molecular weight organic active agents.

In accordance with an example, a bio-chemotronic launcher system comprises: an actuator insert having a plurality of low molecular weight organic active agents, each having a first state in the actuator insert in which the low molecular weight organic active agent is de-functionalized and a second state in which the low molecular weight organic active agent is functionalized for application to a target; a sensor insert having a plurality of sensors each sensor having a first sensor state, wherein the sensor is not active to sense for response data, and a second sensor state, wherein is active to sense for response data; and a controller communicatively coupled to the actuator insert and to the sensor insert, the controller configured to coordinate operation of the actuator insert and the sensor insert by selectively functionalizing certain of the plurality of low molecule weight organic active agents and selectively activating certain of the plurality of sensors according to a protocol.

In accordance with an example, a bio-chemotronic launcher system comprises: a coating containing elements such as but not limited to metallic particles, organic molecules, C60, carbon nanotubes, semiconductors, ultra-small integrated circuits, responsive to external stimuli such as changes in pH, humidity, chemical composition, pressure, shear, electro-magnetic radiation (microwave, radiowave, visible light, ultraviolet light, infrared light, etc.).

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Figure 1:
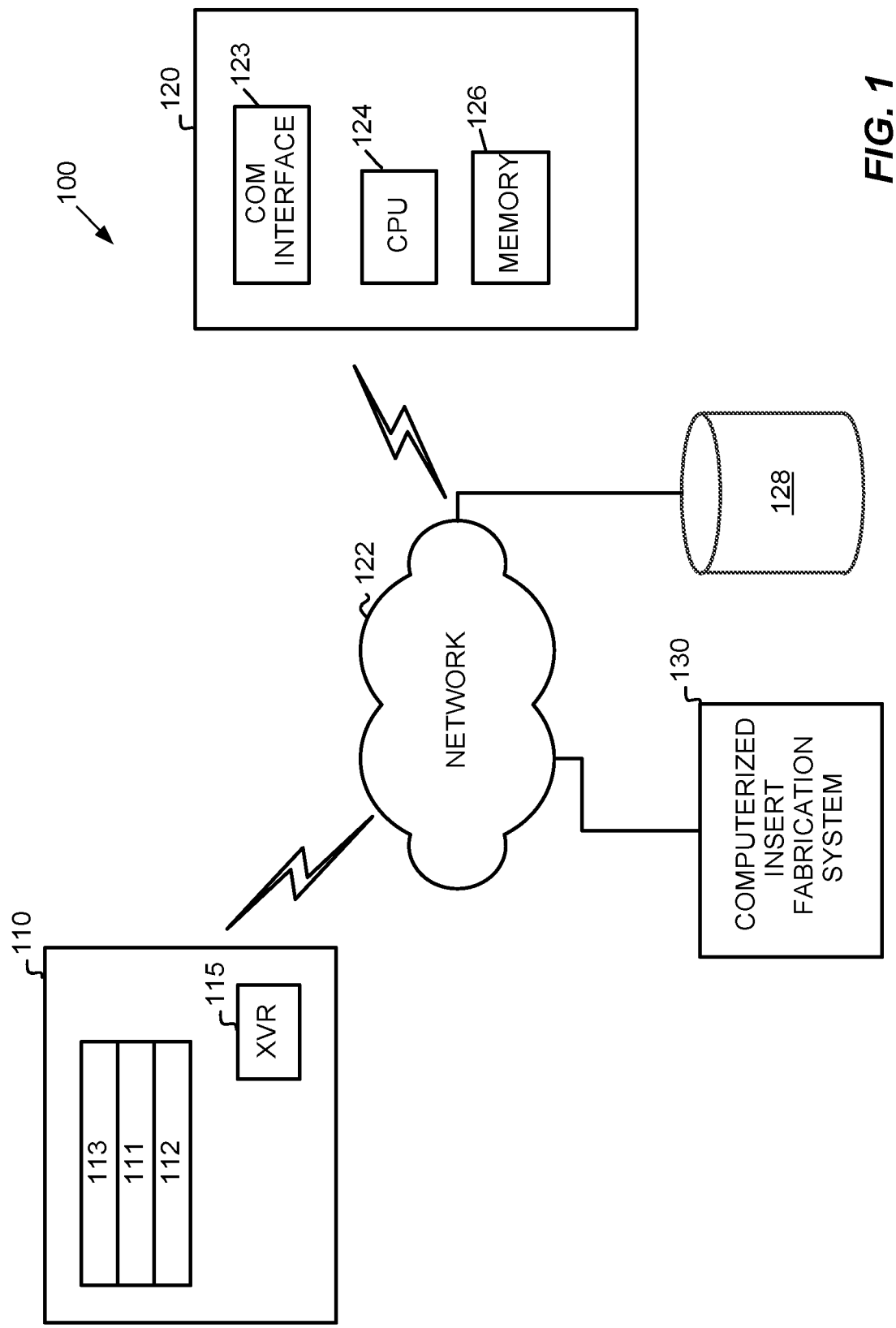
FIG. 1 illustrates a system having a bio-chemotronic insert with an having an actuator insert, a sensor insert, and an integrated controller, in accordance with an example.

Generally speaking, pursuant to these various embodiments, provided is a controllable solid film component and/or device, also termed herein a "bio-chemotronic device," which may be formed of one or more bio-chemotronic layers or inserts. That component and/or device may include a solid film layer structure that includes an actuator insert having one or more low molecular weight organic active agents. The solid film layer structure may further include a sensor insert that includes one or more sensors for measuring a direct or indirect response from a target to the one or more active agents. In some implementations, the sensor is configured to measure the response to external factors, such as presence of biologically active entities, such as allergens, pathogens, pesticides, etc. The actuator insert and the sensor insert may be formed using techniques such as organic vapor jet printing (OVJP), as discussed further herein.

In exemplary embodiments discussed herein below, the solid film structure is an electronically controllable solid film component or device. Control of these solid film structures may be within the structure itself or distributed across the structure and an external structure, such an external controller or sensor. Further still, the solid film structures may be non-electronically-controllable structures, in other examples. For example, the solid film structures may be controlled using embedded temperature triggers (e.g., temperature sensitive components/materials), humidity triggers (e.g., humidity sensitive components/materials), local atmospheric composition triggers (e.g. oxygen-, TNT-, CO-sensitive materials), pressure triggers (e.g. pressure-sensitive adhesive, membrane), shear triggers (e.g. shear-thickening/thinning layer), pH sensors (e.g. indicator dye, acid-/base-triggered dissolving layer), etc. that do not rely upon electronic control.

The actuator insert and the sensor insert may form a combined structure that may also be integrated with a control layer configured to individually control activation of the agents according to a protocol. For example, the control layer may be configured to functionalize active agents for application to the target using a stored and/or predetermined protocol. Example control layers include electronically-controlled layer(s). The control layers herein may be solid film layers embedded with a processor and a memory. The control layers may include addressable electrodes or pads coupled to the processor and capable of receiving control signals that are used to activate regions of an actuator insert layer and/or a sensor insert layer communicatively coupled to those regions, in accordance with executable instructions stored in the memory.

In some examples, the control layers are solid film layers formed of semiconductor structures or ultra-small integrated circuits that are used to control activation of regions. In some examples, the control layers are solid film layers formed of metallic particles, organic molecules, carbon nanotubes, C60 (e.g., Buckminsterfullerene). In these examples, external stimuli or an external controller may be used to control operation of the control layer, thereby providing a distributed control as compared to using an embedded processor and memory.

In yet other examples, the control layer uses one or more temperature-triggered components or materials, humidity-triggered components or materials, local atmospheric composition-triggered components or materials, pressure-triggered components or materials, shear-triggered components or materials (e.g. shear-thinning or shear-thickening materials), and/or pH-triggered components or materials (e.g. an oxide layer that is etched away upon a change in pH). In these example control layers, an external stimulus may be used to control operation of the control layer. For example, with a control layer comprising a plurality of different temperature-sensitive materials, an embedded processor in the control layer or an external inductively coupled antenna may be used to increase or decrease the temperature over an active region corresponding to the temperature-sensitive layer. That change in temperature results in activating an agent in an actuator layer, to release that agent, or to activate a sensor in a sensor layer, or a combination thereof. A pressure-sensitive control layer would use pressure to activate an agent, for example, by applying pressure to a particular location in an actuator insert containing a membrane that bursts, or an electrically conductive elastomer whose conductivity changes upon application of pressure.

Functionalization of the agents in the actuator insert may be achieved in a number of controllable ways. The control layer may activate agents in a time-based manner, a spaced-based manner, or a condition-based manner. Prior to activation, the agents lay dormant in a non-functionalized state, until the control layer activates them. The control layer may be configured to trigger activation based on a timed event, such as at a predetermined time or predetermined time interval, and/or predefined condition. The control layer may be configured to trigger activation based on a space condition, such as distribution of pressure, bioanalytes, lighting, pattern of blood vessels, organ swelling, spatial impact on an organ or a biological system.

In some implementations, the target is a culture of cells on an assay plate; the plate is coated with active pharmaceutical ingredients of interest. The actuator insert (or the entire solid film device) may be configured to conform to the shape of an organ or tissue that may be natural, artificial or a combination of both, while the release of the agents in the actuator insert specific locations on the organ, such as localized inflammation of skin, localized expression of protein, localized increases in the concentration of fluid or ions or other biomarkers. In some implementations, the target is an assay plate, which is coated with an active pharmaceutical ingredient (API) of interest. The actuator insert may be configured to trigger the release of APIs in specific locations of the assay plate. In yet another implementations, the actuator insert is designed as an assay plate cover, where selective locations are coated with one or more low molecular weight organic APIs, released according to a release protocol.

The control layer can be triggered based on a particular sequence of signals, such as sequential order, repeating order, confluence of multiple signals, increasing or decreasing trend in signal, and/or duration of signal(s), such as in response to a simultaneous presence of several biomarkers, or a sustained increase in the detected concentration of a biomarker (e.g. histamine). The control layer may be configured to trigger based on the satisfaction of a condition, such as triggering activation of an agent in response to a sensor detecting a certain event or detecting a certain value. In some examples, activation occurs based on a mode of operation, such as when a bio-chemotronic device is either in a testing mode or a treatment mode. Bio-chemotronic devices in a testing mode may be configured to activate agents according to a predetermined protocol for examining the effectiveness of the agents in generating a responsiveness in a target. Bio-chemotronic devices in a treatment mode may be configured to activate agents according to another predetermined protocol for applying agents to a target to treat a pathology in the target. In example treatment modes, agents may be functionalized in a binary manner, i.e., from a non-functionalized state to a fully functionalized state. In other examples, depending on the agent and/or the controller, functionalization may be from a non-functionalized state to a range of functionalized states. In such examples, the agent may have a gradation of functionalized states that can be controllably activated, as in an analog manner. This second state is also referred to herein as progressive functionalization state.

FIG. 1 illustrates a bio-chemotronic insert system 100 having a bio-chemotronic insert 110 having an actuator insert 111, a sensor insert 112, and an integrated controller 113. The bio-chemotronic insert 110 further includes a transceiver 115 for communicating data to and from an external network-accessible controller 120 via a network 122.

The network-accessible controller 120 comprises a communications interface 123 that communicates over the network 122. The interface 123 may be a wired or wireless interface, where the latter may include a wireless transceiver. The interface 123 may be configured to communicate via communication networks including local and wide-area wireless networks, wired networks, or other IEEE 802.11 or Wi-Fi wireless communication systems, including virtual and extended virtual networks. The present techniques may be applied to any suitable wireless communication system. For example, the descriptions may apply to one or more communication networks that are IEEE 802.xx-based, employing wireless technologies such as IEEE's 802.11, 802.16, or 802.20, modified to implement embodiments of the present invention. In some examples, the interface 123 is configured to communicate as part of a Bluetooth system, Bluetooth Low Energy (BLE) system, WiFi system, beacon-based communication system, or other wireless communication system. The network-accessible controller 120 further includes one or more processors 124 and one or more memories 126 storing computer-readable and computer-executable instructions, such as various instructions described in processes discussed herein.

In the illustrated example, the server 120 is able to access a network-accessible database 128 also connected to the network 122, where that database may store monitored data from a target, genotype data on the target, phenotype data on the target, demographic data on the target, as well as other data, such as environmental conditions (e.g., pollen or smog level). The stored data may be global data such as geolocation data, time of day, calendared event data, proximity to a medical care center data, date of manufacture (in case of artificial tissue or organ) data, and testing methods data. The stored data may be other types of target specific data, depending on the application, such as menstrual/ovulation cycle data, cumulative and/or instantaneous physical activity data, and epidemiological data.

For the bio-chemotronic insert 110, the actuator insert 111 may include one or more agents that may be actuated for delivery to a target. In some examples, actuator insert 111 is a solid film layer structure that includes one or more low molecular weight organic active agents.

The solid film layer structure has a non-functionalized state, in which the one or more active agents are maintained in the layer structure and not actuated for delivery.

The solid film layer structure is configured to have a second state, which is a functionalized state, in which the one or more active agents are functionalized, for example, by stimulation from the integrated controller layer 113. The functionalized state includes the controlled release of the active agent to the target. That controlled release may be to a surface of the target and/or internal to the target, e.g., below the skin surface of a person.

In another implementation, the controlled release is from an object inserted into an assay plate, and/or from a cover of an assay plate into a growth media containing a target cell, organoid cultures, etc. In such implementations, the bio-chemotronic insert includes the actuator insert as a cover of an assay plate and/or cover and further includes the assay plate base as a target, where that target insert may contain target cells, organoid cultures, etc.

While a solid film layer structure is described as having a non-functionalized state and a functionalized state, in some examples, the active agents themselves have these states. For example, with the present techniques, actuator inserts 111 may be formed having multiple different active agents and controller layers 113 may be configured to individually functionalize these different agents, such that a first agent is functionalized, while the other agent or agents remain non-functionalized. As such, references herein to the solid film layer structure having a first state and a second state, include examples, where the individual active agents themselves have individually (or collectively) controllable first and second states.

The actuator insert 111 may be a patterned structure containing multiple active agents. For example, the actuator insert 111 may have multiple thin layers each layer having a different active agent embedded in each thin layer, with each layer individually controllable by an actuator and controller 113 to selectively release a respective active agent to the target. This patterning may be achieved in other manners.

In some examples, the patterning of the actuator insert 111 is achieved by having different active agents positioned at different locations in a single solid film layer. The controller 113 may then be used to activate the desired agent at a particular location. This configuration is particularly useful in bio-chemotronic dosage assays, where the bio-chemotronic insert 110 is used to test different dosage levels of the same treatment agent on a target, in order to identify the most responsive treatment dosage.

Figures 31A, 31B:
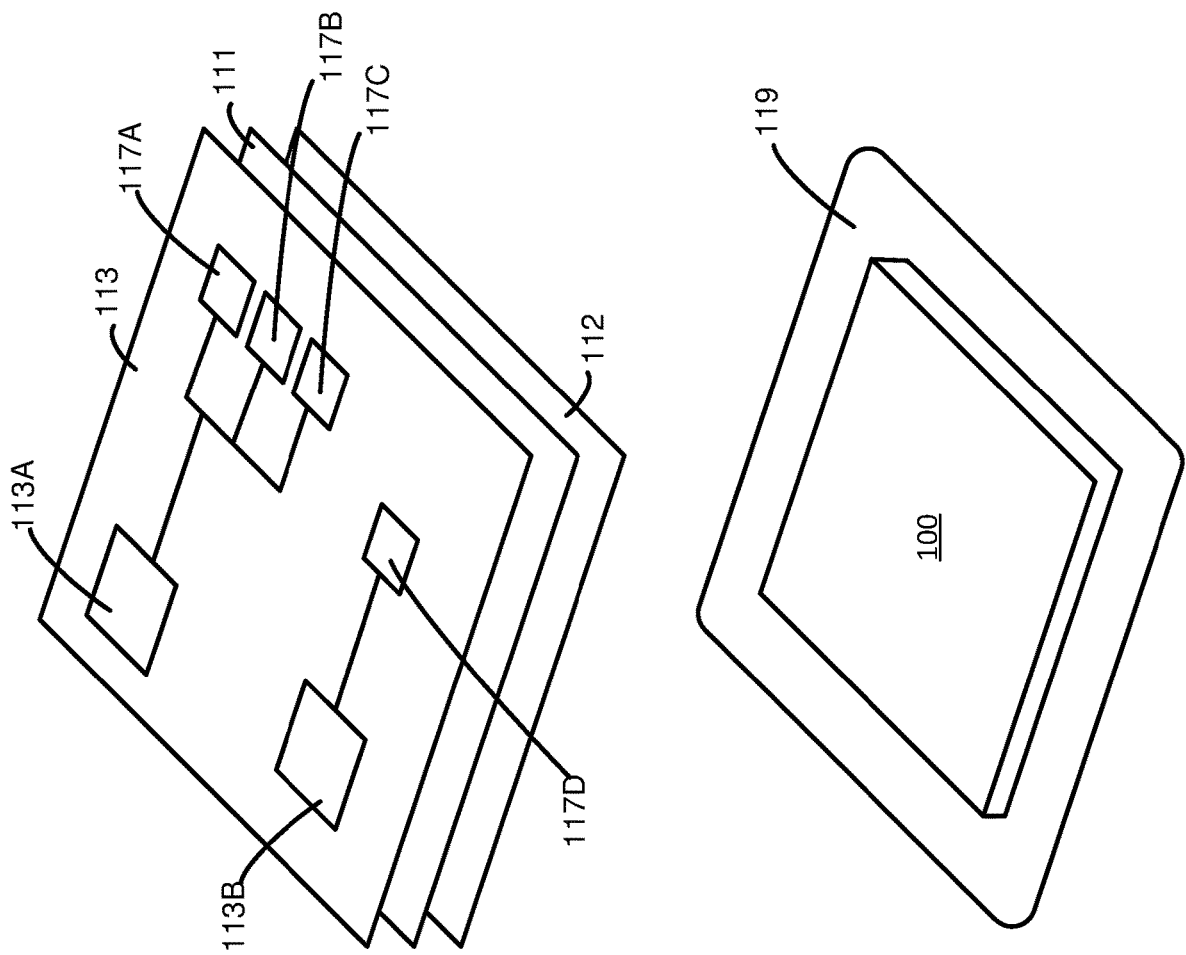
FIGS. 31A and 31B illustrate an example implementation of a bio-chemotronic insert system of FIG. 1, implemented as a wearable bio-chemotronic structure, in accordance with an example.

As discussed herein, the controller layer 113 may comprise one or more controllers, electronic controllers or non-electronic controllers. The controllers may include processors with memories and activation pads or electrodes. The controllers may be powered at the controller layer 113, for example, through a battery or other power source therein. In other examples, the controllers may be powered inductively. The controllers may include temperature controllers (e.g. a temperature-sensitive material), humidity controllers, local atmospheric composition controllers, pressure controllers, shear controllers, pH sensors, etc. that do not rely upon electronic control. The controllers may be formed of semiconductor structures or ultra-small integrated circuits. In some examples, the control layers are solid film layers formed of metallic particles, organic molecules, carbon nanotubes, C60 (e.g., Buckminsterfullerene) that form the controllers. FIGS. 31A and 31B illustrate an example of the bio-chemotronic insert system 100, in exploded and fabricated form, implemented as a wearable patch, and showing a plurality of controllers embedded in the controller layer 113. As shown in FIGS. 31A and 31B, the controller layer 113 includes two different types of controllers 113A and 113B, where controller 113A is electrically coupled to activation pads 117A, 117B, and 117C, and controller 113B is electrically coupled to activation pad 117D. The fabricated device is shown in FIG. 31B, showing the bio-chemotronic insert 100 formed in an adhesive application pad 119 for affixing the insert 100 to the surface of the skin.

In some examples, the patterning of the actuator insert 111 may be achieved by co-locating active agent pairs or groupings in the solid film layer. In such examples, the bio-chemotronic insert 110 may be used to identify potential interactions between a first active agent, acting as the main agent, and a secondary (co-located) test agent. Such patterning configurations may be used to provide a progressive increase in concentration of an active agent, such as by controlling the release of a progressively more active agents in a general location of the actuator insert 111, until a desired concentration of agent release into the target has been achieved.

We note that the patterning of the actuator insert 111 may be a combination of these examples, i.e., some inserts may have multiple layers and different active agents in different locations, for example.

With the direct, additive printing approaches described herein, including organic vapor jet printing (OVJP), we can vary the thickness across any of layers herein, as well as how many layers are stacked, where those layers are positioned on a substrate. The thicknesses of the various layers described herein may depend on the amount of material (active agent) to be delivered and/or used for sensing, the available area, the release schedule, the desired morphology (for example, obtaining "nanolobes" sometimes requires some minimum thickness to be deposited), and the thickness tolerated by the application (e.g. a subdermal implant or a buccal patch should not be too thick, so as to not cause discomfort in ordinary use). Location can also determine thickness; in some implementations, deposits made on an assay plate vary in thickness depending on the location on the plate and target cell culture. Similarly, deposits made over certain actuators or sensors in some applications need to form a continuous layer, while others tolerate a discontinuous layer. More potent versions of an active agent, for example, enable smaller thickness values.

The sensor insert 112, like the actuator insert 111, may have a solid film layer structure containing one or more sensors. The sensors may be of different category types, including chemical sensors, temperature sensors, bioanalyte sensors, optical sensors, electrical sensors, pressure sensors, pH sensors, motion sensors, vibration sensors, sound sensors, accelerometers, location sensors, and others. Example sensors include sensors configured to sense for specific chemical compounds, glucose sensors, blood oxygen sensor, circulating tumor cells monitors, genetically active compound sensors (e.g. DNA), natural or artificial compound biomarkers, ion sensors, etc..

Figure 2:
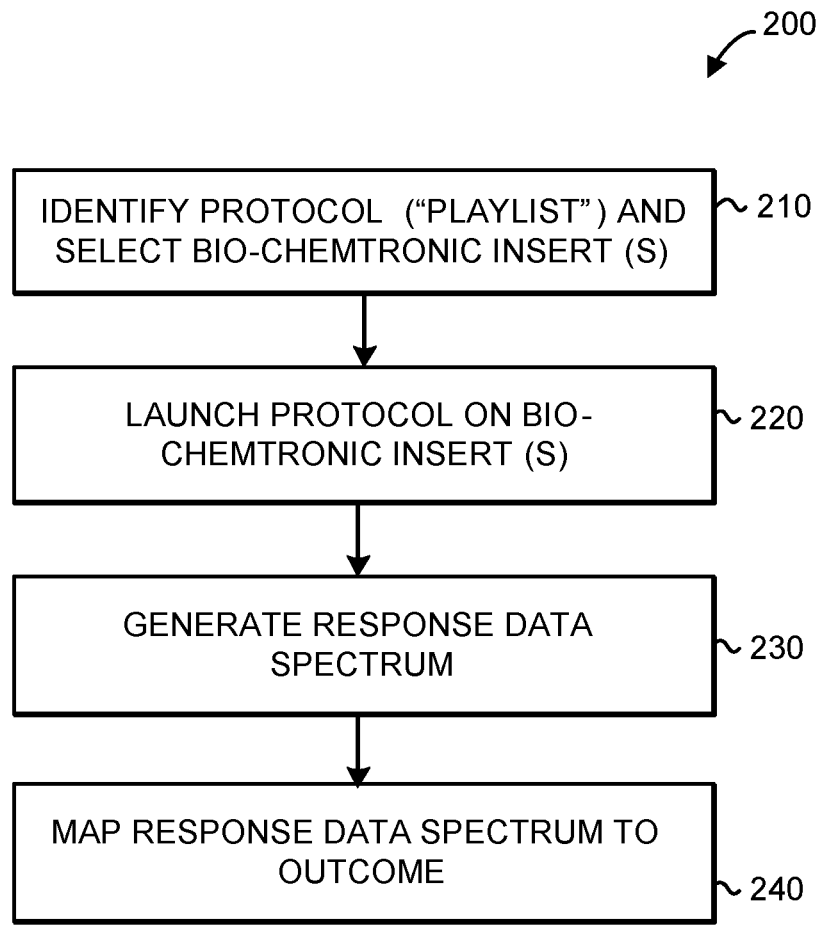
FIG. 2 illustrates a process for launching a protocol on the bio-chemotronic insert system of FIG. 1, in accordance with an example.

FIG. 2 illustrates a process 200 that may be executed by the bio-chemotronic insert system 100. At a block 210, a bio-chemotronic insert is identified according a desired protocol (or "playlist"). This identification may be based on target data such as body temperature, heart rate, blood oxygenation level, allergic reaction, blood pressure, fingerprint, retina image, tissue construction, etc. Other data that may be used to identify a particular type of bio-chemotronic insert, including whether the bio-chemotronic insert is to be a single agent insert or a multiple agent insert. Examples include an insert used for dispensing an anti-histamine, a blood pressure medication, a antidepressant, and/or a diuretic. Further example inserts would be used for sensing the presence of an allergic response, the presence of vaso-dilating or vaso-constricting compounds, the present of caffeine, and/or the presence of alcohol. Yet further example inserts would measure poison levels or inactive cosmetics agent. In any of such examples and others which protocol and associated bio-chemotronic insert is selected at block 210 may be based on the data stored in the database 128. That data may include information on, by way of example, geolocation information, release rate prescribed for the user, manufacturer and batch information, phenotype, environmental conditions (pollen or smog level), geography, time of day, calendar events, menstrual/ovulation cycle, cumulative and/or instantaneous physical activity, epidemiological data, proximity to a medical care center, date of manufacture (in case of artificial tissue or organ), and testing methods.

With the bio-chemotronic insert identified, the corresponding protocol is launched at block 210. The protocol may be stored in the network-accessible server 120 and communicated to the bio-chemotronic insert 110 over the network 122 during user or the insert. In other examples, the protocol may be fully or partially embedded within the bio-chemotronic insert, for example, stored in the controller layer 113. The types of protocols may vary. In some examples, the protocol is a testing protocol used to determine the condition of the target or used to examine the possible efficacy of different dosages of a drug delivered to the target. In other examples, the protocol may be a treatment protocol, which is used to treat a target identified as having a treatable condition.

In operation, with the bio-chemotronic insert 110 engaged to the target, the insert 110 executes the protocol at block 220. In the example of a dosage assay bio-chemotronic insert, the protocol may include instructions on testing different dosage levels of an active agent on a target. In such an example, the bio-chemotronic insert 110, in particular the controller 113, begins testing a dosage regimen, by functionalizing an active agent at a first dosage level for administration to the target, e.g., through a diffusion or other delivery mechanism. The insert 110 may continue executing the protocol, for example, by next administering the active agent at a second dosage level, and so on. In yet other examples, the protocol may include a second state that is a progressive functionalized state. With progressively functionalizable agents, the same agent may be functionalized over a range of states, for example, over a range of possible dosage levels. Indeed any references herein to a functionalized state, contemplate progressively functionalizable agents as well.

In the example process 200, at block 230, the bio-chemotronic insert 110 generates data representative of a spectrum of target responses to the functionalized active agent (i.e., a response data spectrum). That response spectrum data is generated by one or more sensors in the sensor insert 112. The controller 113, for example, after functionalizing the active agent awaits data from a sensor in the sensor insert 112. In the example of a dosage assay bio-chemotronic insert, the sensor may measure for a bioanalyte response in the target, for each released dosage. The sensor communicates the measured response data to the controller 113, e.g., through an electrical connection to controller 113. To generate an entire response spectrum, the controller 113 may execute the entire protocol. In the example of a dosage assay bio-chemotronic insert, that means applying each active agent dosage called for in the protocol until the required active agents have been functionalized and sensed by the bio-chemotronic insert. The entire response data for the protocol is collected through the block 230.

After the response spectrum is completed, at a block 240, the response spectrum is mapped to a biological and/or therapeutic outcome, such as secretion of compounds, apoptosis, mitosis, a reduction in the level of histamine, the presence of vasodilation, decrease in heart rate, increase in blood flow, the presence of hormone activity, or other quantifiable symptoms. In some examples, this mapping occurs at the network server 120. For example, the insert 110 may communicate the spectrum of response data from block 230 to the network server 120, which may have stored mapping algorithms for analyzing the response spectrum. Applying mapping algorithms, the network server 120 assesses a condition of the target, such as for example, stage of cell cycle, an allergy profile of the target, the phenotype of the target, tissue condition, cancer stage, physical fitness, artificial organ service life parameters, etc. In some examples, the analysis produces an assessment metric of the condition of the target. In some examples, the analysis produces a treatment regimen for the target based on the condition of the target.

Figure 3:
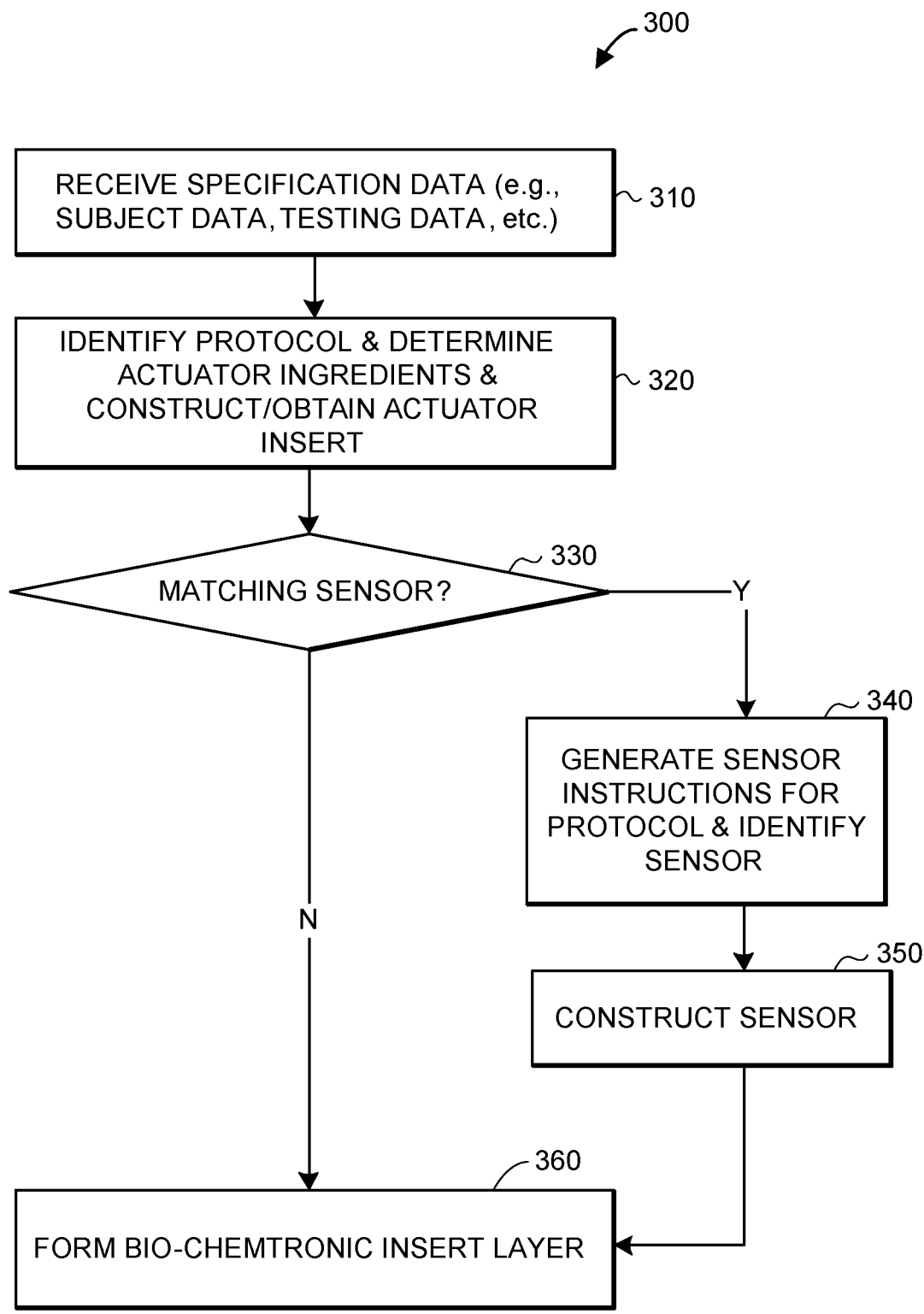
FIG. 3 illustrates an example process for configuring a bio-chemotronic insert to have a protocol, in accordance with an example.

An example implementation of the protocol identification block 210 is illustrated in FIG. 3 as example process 300. At a block 310, a specification is provided to the network server 120. The specification may identify, by way of example, a set of desired applications, target parameters, authenticity, integrity, absence of tampering, and execution time-frames. The network server 120 analyzes the specification and determines a protocol and one or more active agents that are to be used to compose or produce the actuator insert 111 for executing the protocol. The network server 120, at block 320, then sends instructions to a manufacturing stage 130 (see, FIG. 1) for assembling the bio-chemotronic insert, including the actuator insert 111. Additionally, at the block 320, the network server 120 produces instructions for the protocol to functionalize the active agents in the actuator insert 111, where those instructions may include target specific instructions, as well as default instructions for a sensor to use in monitoring a targets response to be active agents.

At a block 330, the network server 120 determines whether a matching sensor insert should be used with the actuator insert 111. If a matching sensor insert is to be used, then control is passed to a block 340 where sensor instructions are generated, and then to a block 350 where the sensor insert 112 is generated by the manufacturing stage 130, in response to received instructions from the network server 120. Whether a sensor insert is to be generated (e.g., at block 350) or not, control is eventually passed to block 360, where actuator insert 111 and (optional) sensor insert 112 are packaged to generate the bio-chemotronic insert 110, in accordance with examples further described herein.

Further still, this bio-chemotronic insert 100 may include the protocol instructions for the bio-chemotronic insert. These instructions may include instructions for functionalizing the actuator insert 111, instructions for monitoring the use of the actuator insert 111, instructions for using the sensor insert 112, instructions for authenticating insert 111 and/or insert 112, and instructions for monitoring the operation of the sensor insert 112. In some examples, the bio-chemotronic insert may further include instructions for providing a treatment for therapy to the target in response to sensor data. In this implementation, these stored data and instructions comprise a protocol of operation for the bio-chemotronic insert or a matching set of inserts.

Figure 4:
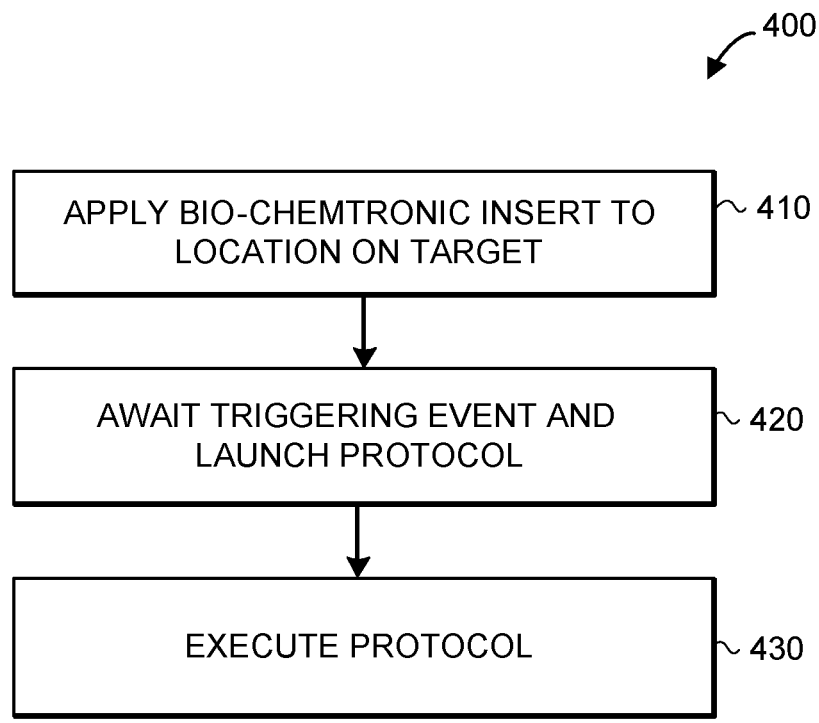
FIG. 4 illustrates a process for using a bio-chemotronic insert according to a stored protocol, in accordance with an example.

FIG. 4 illustrates a process 400 for using the bio-chemotronic insert according to a stored protocol. At a block 410, the bio-chemotronic insert is received and applied to the target. As discussed further below, the bio-chemotronic insert may be produced in any number of different form factors. These include, a wearable patch, a patch that may be attached to the target via a wristband, armband or other attachment mechanism, or glue, or a rectal insert, buccal patch, a cover for a multi-well plate, etc.

At a block 420, a stored protocol is launched, for example, in response to a signal from the network server 122 received at the bio-chemotronic insert or in response a time-based trigger or other trigger at the bio-chemotronic insert. The trigger changes the state of the bio-chemotronic insert from non-functionalized to functionalized, including progressive functionalization. The bio-chemotronic insert executes the protocol, and at a block 430, the protocol is started, for example, with the controller 113 functionalizing a first identified active agent through an actuator.

Figure 5:
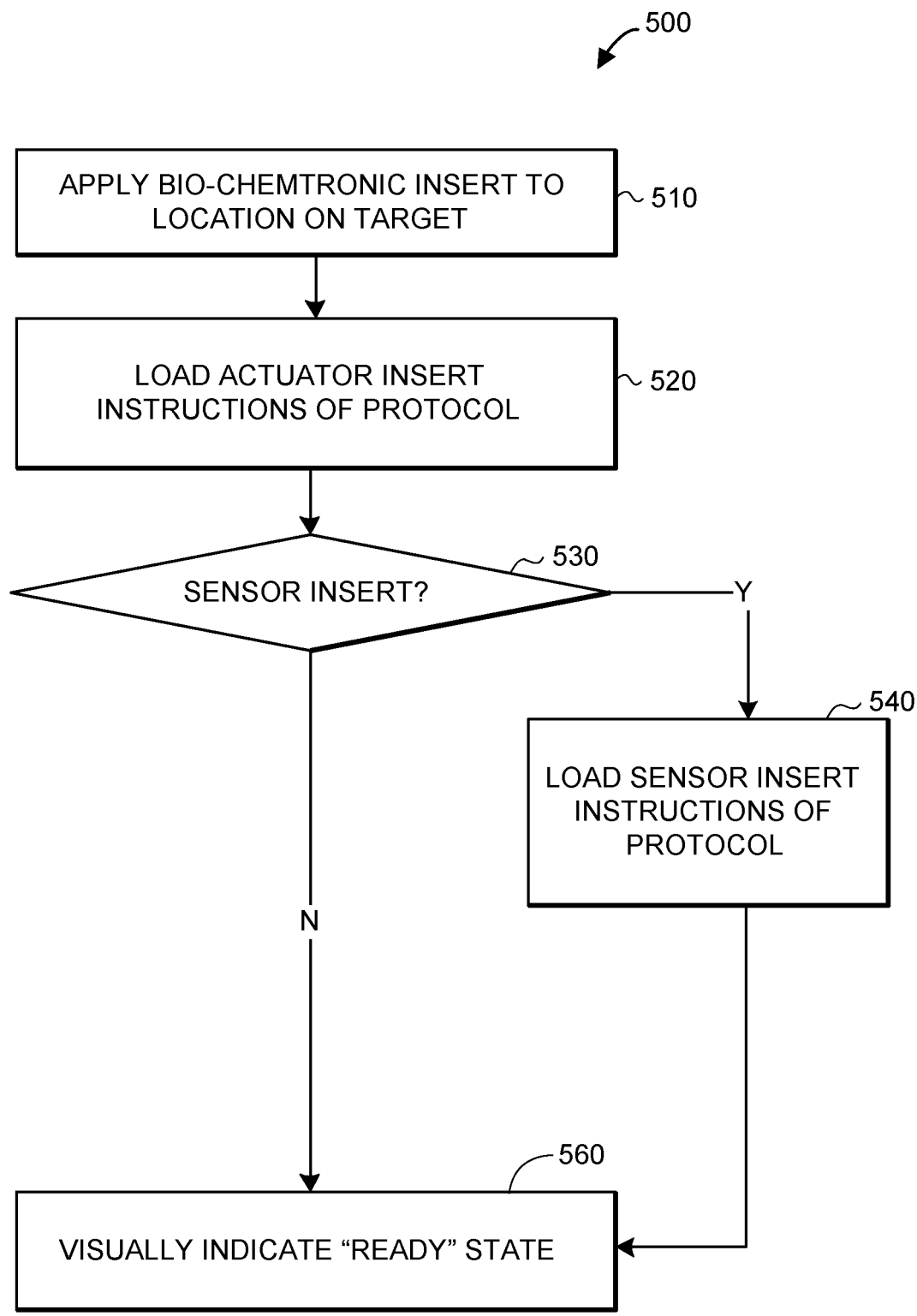
FIG. 5 illustrates a process for launching a protocol using a bio-chemotronic insert system, in accordance with an example.

To launch the protocol, the controller 113 may perform the process 500 as shown in FIG. 5. For example, at block 510, the bio-chemotronic insert, and in particular the actuator insert 111, is applied to a target. The controller 113 loads instructions for functionalizing the actuator insert 111, at a block 520. At a block 530, the controller 113 determines if a sensor insert 112 is present. If no sensor is present, then the controller 113 enters a ready state, which may be indicated to the end user or controlling system by, for example, visual, auditory, or data signal. In this example, the bio-chemotronic insert 110 has a ready state that indicates to the user the that insert 110 is ready for operation. In other examples, the insert 110 may begin the protocol automatically, e.g., based on the settings of the control layer 113 or external conditions.

If a sensor insert 112 is present, then at block 540, instructions for operating the sensor insert 112 in accordance with the protocol are loaded for execution by the controller 113. In some examples discussed further, an actuator insert and a sensor insert may be separately positioned in place and, in such examples, the process 500 may further determine if the sensor insert is positioned in place, before loading the sensor protocol instructions.

Figure 6:
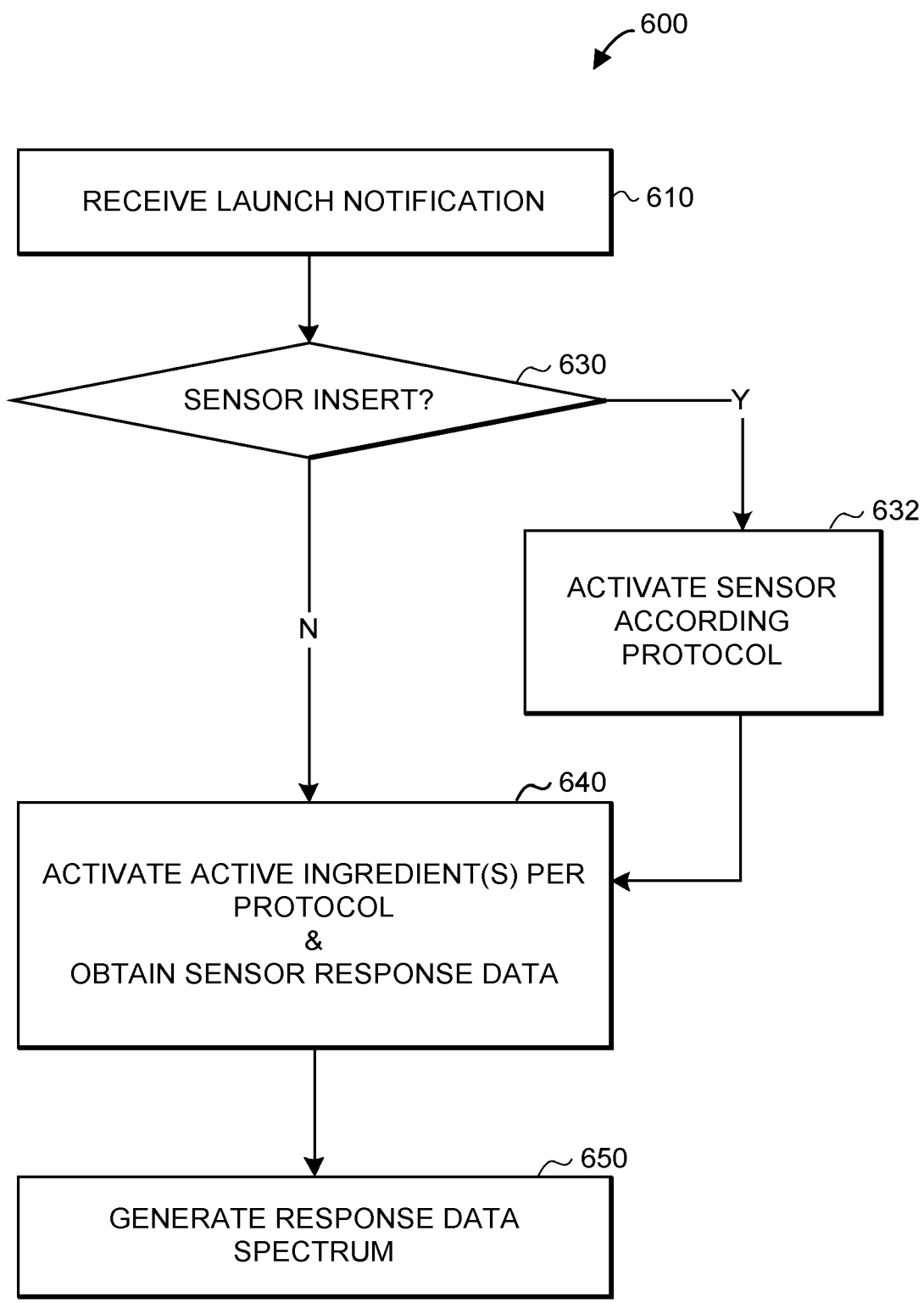
FIG. 6 illustrates a process for generating response spectrum data using a bio-chemotronic insert system, in accordance with an example.

In FIG. 6, an example implementation of the generation of a response spectrum of block 230 is shown as example process 600. At a block 610, the controller 113 receives a launch notification instruction from the network server 122. From that launch notification, the controller 113 begins the active agent functionalization, per a stored protocol. The controller 113, at block 630, determines if a corresponding sensor has been identified per the protocol. If yes, at a block 632, the controller activates the corresponding sensor in the sensor insert 112 according to the stored protocol instructions. Control is passed to a block 640, which then performs the functionalization of the active agent and the sensor operations to record response data from the target, i.e., data recorded as consequence of the target being exposed to the active agent. Data from the block 640, in particular the response data from the sensor insert 112, is then provided to the block 650, which generates the response spectrum. In one implementation, the spectrum comprises a series of data representing the level detected of one or more agents as a function of time, or a bioanalyte corresponding to the metabolism of an active agent.

Figure 7:
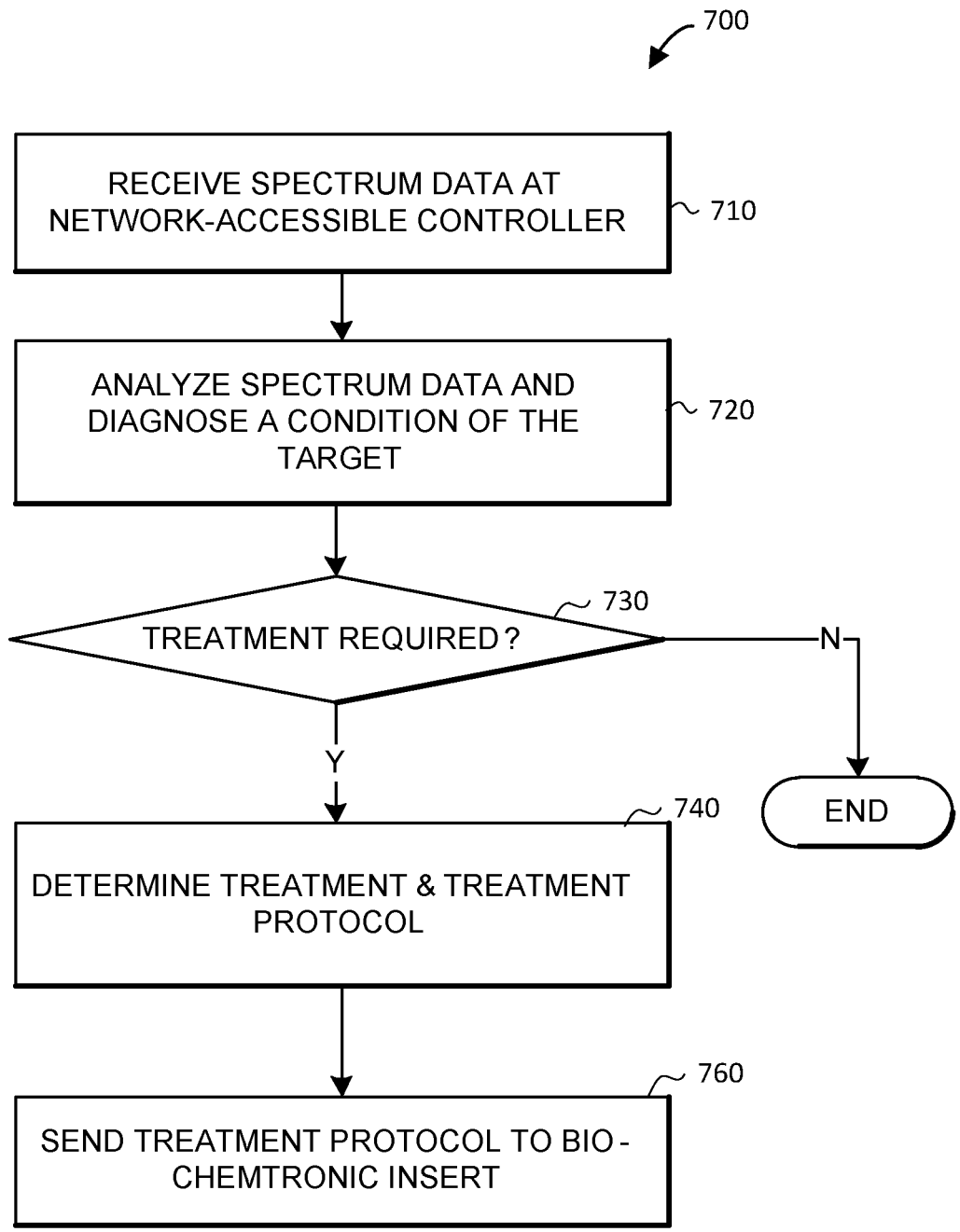
FIG. 7 illustrates a process for mapping response spectrum data to diagnosing a condition of a subject and determining a treatment or treatment protocol, in accordance with an example.

A process 700 for mapping a spectrum to an outcome, as may be performed by the block 240, is illustrated in FIG. 7. In the illustrated example, at a block 710, response spectrum data is received at the network server 122, which then performs a condition diagnosis at block 720. Based on that condition diagnosis, the network server 122 determines whether a treatment is required for the target, at the block 730. The network server 122 identifies the corresponding treatment for prescribing to the target at the block 750. After the prescribed treatment is initiated at the block 750, the network server 122 sends instructions to the bio-chemotronic insert in the form of a treatment protocol, via block 760. The bio-chemotronic insert may then execute the treatment protocol.

Figure 8:
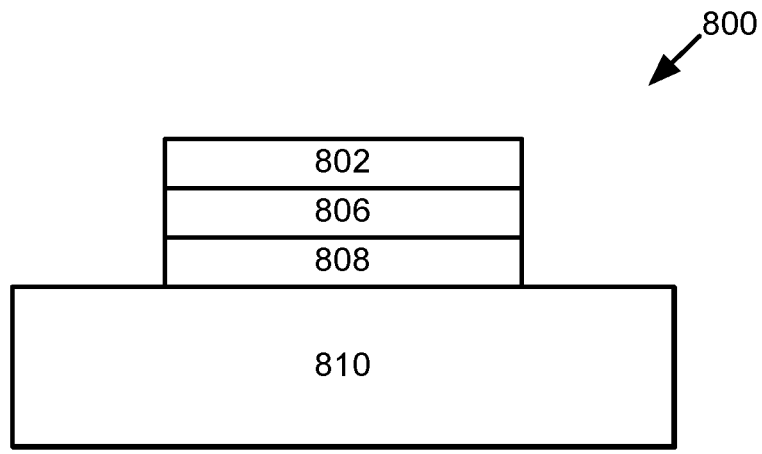
FIG. 8 illustrates an example bio-chemotronic insert, in accordance with an example.

An example bio-chemotronic insert 800 is shown in FIG. 8. The bio-chemotronic insert 800 includes a control layer 802, an insert layer structure 806, and a body interface 808, which interfaces with a target 810. As discussed in various examples herein, the control layer 802 may include a processor, a memory, and a transceiver that allows a controller to control operation of the bio-chemotronic insert, for example to control the functionalization the active agents and to control the operation corresponding sensors, as well as to control communications an external controller, such as the network server 122. The insert layer structure 806 may include one or more actuator inserts, such as the actuator insert 111, and in some examples will further include one or more sensor layers, such as the sensor insert 112. The body interface 808 is an example of an interface layer for applying the insert 800 thin film device to a target. The interface layer may be implemented through many different form factors, including, for example, as an adhesive layer of a patch containing the insert 800, where the adhesive layer applies the patch to the skin or a subject. The interface layer may be the contact layer for strap mountable device, such as using the insert 800 has part of a wearable device, such as a wearable watch or wristband. In these examples, the interface layer may be a non-adhesive bottom contact layer of the wearable device. In yet other examples, the interface layer may be the contact layer for a handheld, mobile device that is held adjacent to a subject for operation of the insert 800. Yet, other example form factors and interface layers may be used.

The body interface layer 808 may be formed of multiple sub layers, for example each having a different material enabling biocompatibility, filtering, switchable filtering, stimulation of a service of the target, etc. Examples of biocompatible materials that may be included in the body interface 808 include poly(3,4-ethylenedioxythiophene) polystyrene sulfonate (PEDOT:PSS), parylene C, gold, copper, stainless steel, poly(lactic-co-glycolic acid) (PLGA), silicone, etc. Examples of filtering materials that may be used in the body interface 808 include nanoporous anodic alumina, porous polyethylene, GoreTex, etc. Examples of switchable filtering materials include pH-sensitive integral asymmetric polystyrene-b-poly(4-vinylpyridine) (PS-b-P4VP) diblock copolymer membranes with temperature-responsive poly(N-isopropylacrylamide) (pNIPAM), and PPy/PVDF membrane, silica-poly(N-isopropylacrylamide) hybrid membranes (see, e.g., Wu Y et al., Polypyrrole based switchable filter system, Conf Proc IEEE Eng Med Biol Soc. 2007; 2007:4090-1,).

Figure 9:
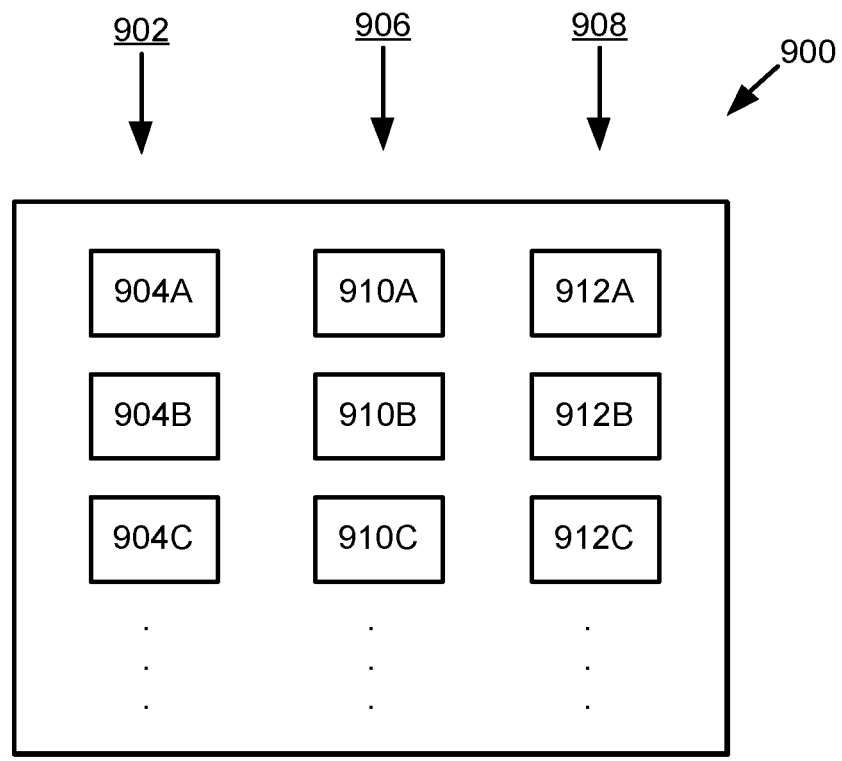
FIG. 9 illustrates an example actuator layer of a bio-chemotronic insert and having multiple active agents, in accordance with an example.

FIG. 9 illustrates an example actuator layer that maybe part of the insert layer structure 806. As illustrated, actuator layer 900 includes a plurality of different active agents. In the illustrated example, the active agents are configured into rows, where each active agent corresponds to a different position in a row. A first row 902, for example, includes active agents 904A, 904B, 904C, etc. where each of these agents may have an entirely chemical structure, or where each may represent the same active agent by maintained in different dosage levels, or some combination thereof. As with any of the examples herein, these active agents may be activated in response to and thereby under the control of a control layer, whether an electronic or a non-electronic control layer.

In the illustrative example of the active layer 900, each row may represent a different protocol. That is, row 902 may correspond to a first protocol, while a second row 906 may correspond to a second protocol, and a third row 908 may correspond to third protocol, and so on. For each of these rows, a corresponding different set of active agents are provided, which may be individually or collectively, for example in a sequential or a parallel manner may be applied to a target for sensing the target response to be selective protocol. In the illustrated example, row 906 corresponds to a protocol defined by active agents 910A, 910B, 910C, etc. The third row protocol 908 corresponds to an active agent regimen that includes active agents 912A, 912B, 912C, etc.

In some examples, the active layer 900 may instead represent a single protocol bio-chemotronic insert, in which each active agent in a row is functionalized at the same time, and where the rows are then functionalized individually, in a sequential order. In this example, the active agents 904 would be functionalized at the same time in a first protocol step. After that first protocol step, sensor in the sensor insert will record response data from the target. After that time, a second application of active agents is performed, specifically by performing a second protocol step that includes functionalizing active agents 910 in row 906. Correspondingly, third protocol step would follow after response data is collected from sensors in response to the second protocol step, thereby functionalizing row 908.

Figure 10:
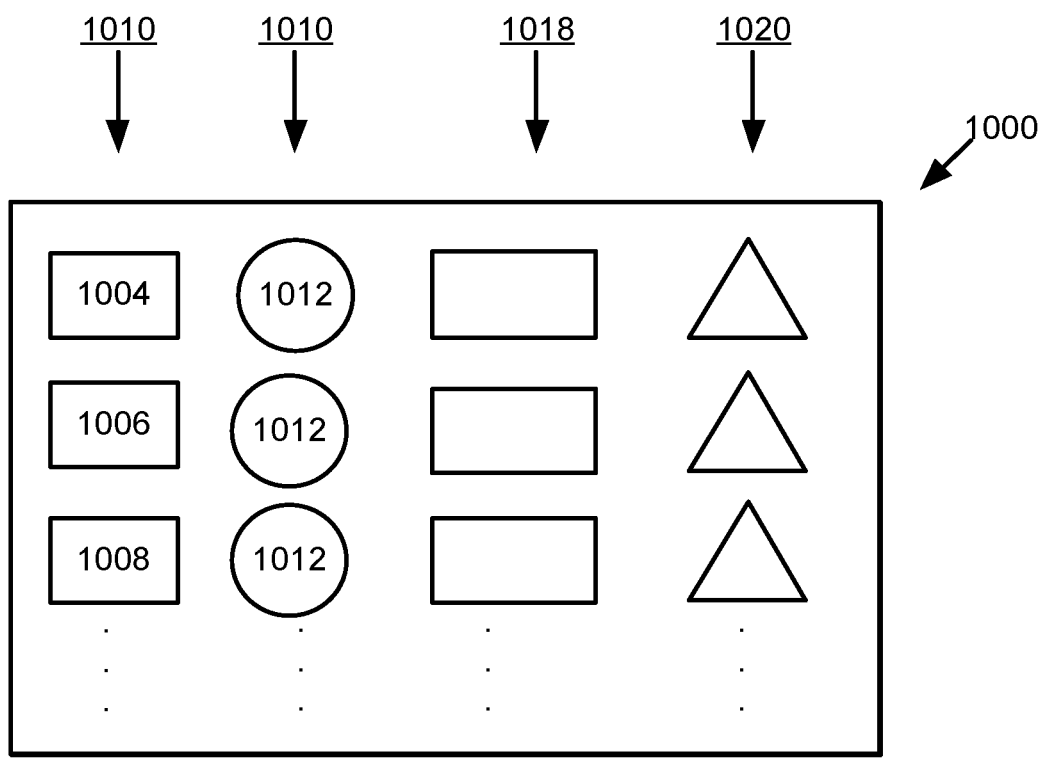
FIG. 10 illustrates an example actuator insert and sensor insert integrated into the same layer structure of a bio-chemotronic insert, in accordance with an example.

FIG. 10 illustrates another example of the insert structure 806. Unlike FIG. 9, in FIG. 10 an insert structure 1000 integrates an active insert and sensor insert into the same layer structure. A first row 1002 contains a plurality of active agents 1004, 1006, 1008, etc., which form a first active agent protocol step. The second row 1010 is configured as a sensor insert row, having sensor elements 1012, 1014, 1016, etc. Each of these sensors corresponds to one of the active agents in the row 1002. This integrated configuration can be repeated with additional roles in the same layer 1000, for example, with row 1018 corresponding to a second active agent protocol, and row 1020 corresponding to a second set of sensors.

Figure 11:
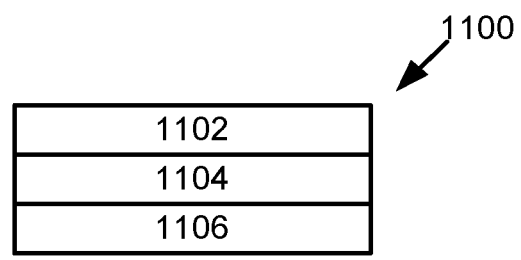
FIG. 11 illustrates another example actuator insert, in accordance with an example.

FIG. 11 illustrates another example actuator insert 1100 that may be used as part of the insert layer structure 806. The actuator insert 1100 includes a combination of different actuator sub-layers 1102, 1104, and 1106. These sub-layers may include different active agents. While in some examples, these sub-layers may include barrier coatings, matrix materials, tracer compounds, getters, buffer, or luminescent compounds. The barrier coatings are designed to prevent the diffusion of certain entities (e.g. oxygen, moisture, ions, etc.), and may include parylene, silicon oxide or nitride, graphene, polyimide, metallized polyethylene, engineered membranes, etc. The matrix materials are designed to stabilize and/or disperse the active agent, facilitate or delay dissolution, etc., and may include PLGA, PLA, and/or combinations thereof. The membranes may also contain channels distributed to be substantially in the plane of the membrane, themselves distributing pressure, temperature, fluid, gas, and/or electrical and/or sound signals.

Figure 12A:
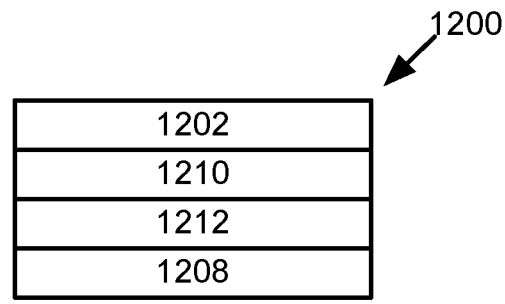
FIGS. 12A and 12B illustrate an example bio-chemotronic insert in the form of a travel kit bio-chemotronic insert device, in accordance with an example.
Figure 12B:
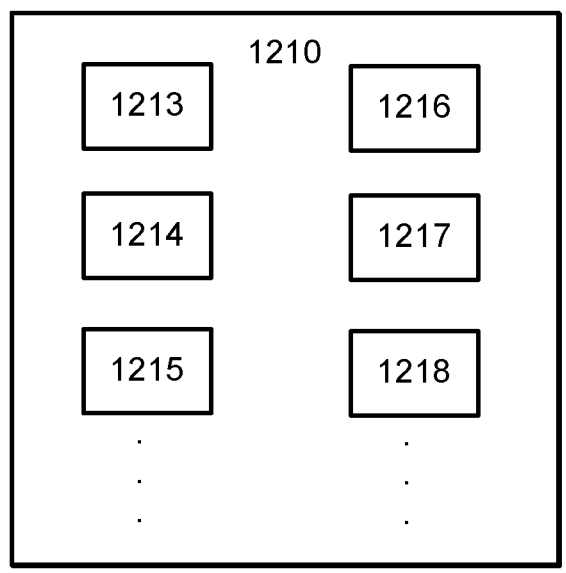

FIGS. 12A and 12B illustrate an example bio-chemotronic insert in the form of a travel kit bio-chemotronic insert device 1200. In the illustrated example, a bio-chemotronic insert is formed with an integrated actuator insert and sensor insert, similar to that of FIG. 10. Travel kit 1200 includes a control layer 1202 an insert layer structure 1206, and a body interface 1208. As discussed in other examples herein, the insert layer 1206 may include chemicals and/or generate impulses. The insert 1206 may include an actuator insert 1210 and a separate sensor insert 1212. As discussed, in some examples the actuator insert 1210 is separate from the sensor insert 1212, while in other examples the two layers are integrated together. This latter configuration maybe used to provide localized triggering and sensing of specific locations on the target, e.g., as may be useful in assessing circulation at a particular location or metabolic response at a particular location. In the illustrative example, the actuator layer 1210 contains a plurality of different active agents 1213, 1214, 1215, 1216, 1217, 1218, etc. These active agents, for example, may include in no particular order melatonin, antihistamine, ibuprofen or some other active agent for pain relief, indomethacin functioning as a non-steroidal anti-inflammatory, or any other active agents as may be desired in a travel kit. Wherein more potent variants of an ingredient may be desirable for insert miniaturization purposes. In this way the actuator insert 1210 is a multi-active agent layer structure that maybe used to apply any one or more of these active agents to a target, in response to a protocol.

In some examples, which active agent or agents is functionalized may be determined in response to response data collected from by the sensor insert 1212. For example, the sensor insert 1212 may include a plurality of different sensors each responding to one or more the active agents of the actuator insert 1210. In the illustrated example, just as a matrix array of active agents is positioned at different locations in the insert 1210, a matrix array of sensors may be positioned at different and corresponding locations in the sensor insert 1212. These agents and sensors maybe logically grouped in the inserts according to different applications i.e. according to different protocols.

For a travel kit, those protocols may be based on different physiological outcomes desired from a single insert. The device 1200 may have stored (i) a protocol for providing a sleeping aid, (ii) another protocol for providing allergy management, (iii) another protocol for providing alertness, and (iv) another protocol for providing information response. In some examples of those protocols may be linked together, such that one protocol necessarily accompanies, follows, or precedes another protocol. For example a protocol may call for the release of one more active agents that include an antihistamine. However because antihistamine functionalization can be linked with causing drowsiness in a target, a second protocol maybe associated with the release of the antihistamine, such as a melatonin releasing protocol. In such examples the melatonin protocol maybe performed automatically after an antihistamine protocol is performed. Or in other examples and antihistamine protocol maybe performed, after which a sensor senses whether a histamine response can be detected in the body, from which the control layer 1202 may determine that a melatonin protocol is to be entered.

It is noted that the body interface 1208 may provide both a barrier that blocks active agents from contacting the target, as well as serving as a permeable or semi-permeable membrane between the insert and the target. The body interface 1208 may be implemented in various ways. In an example, the body interface 1208 may include one or more openings created to access bodily tissue or fluid, e.g., to release a micro dose of active agent upon functionalization. In other examples, the body interface 1208 may include an opening that admits a bioanalyte into the interface 1208, where a sensor detects the bioanalyte. In another example, an opening may be present in the body interface, and sealed using a sealing mechanism, such as the collection of blood cells or other moieties generated in the body as a clotting response to the delivery of the active agent to the target. This type of sealing mechanism is a naturally occurring sealing mechanism detectable by a sensor in the sensor layer 1212. In other examples, an artificial sealing mechanism may be used, such as a polymer substance that forms a seal under exposure to air or to a bodily fluid.

In some examples, the body interface 1208 may be activated as a rapid response to a stimulus. An example rapid response bio-chemotronic insert is a bulletproof patch or garment, which releases a pain relief active agent upon impact from a projectile. For example, the bio-chemotronic insert may include a triggering sensor that sensing an impact and triggers a controller in the layer 1202 to functionalize release of a pain relief agent in the insert 1206. While triggering may be based on a separate triggering sensor and while a controller may be used, in other examples, triggering and release of is performed within the insert 1206, without electronic control. For example, an impact may change the structure of the insert 1206 in the bio-chemotronic insert 1200, including body interface 1208, such that an active agent is released as a result of the change in structure. That active agent is then released to contact the target. In another example bio-chemotronic insert, the body's response, such as a change in moisture level of the skin or a change in electrochemical signals in the body may trigger the release the active agent.

As described, the present techniques describe a bio-chemotronic insert with an active substrate that is controllable using an integrated electronics layer with a controller capable of executing a testing protocol using the bio-chemotronic insert. The protocol contains instructions functionalizing active agents to be applied to a target, as well as instructions for sensing response data indicating the target's response to the active agents. In other words, an integrated controller can change the state of an insert to switch one or more active agents from a non-functionalized state to a functionalized state. That switch may occur upon instruction from an external controller, such as via an activation signal received from a network-accessible server. In some examples, the switch occurs based on a triggering event sensed on the bio-chemotronic insert, without communication to/from an external controller. In some examples, the switch occurs in response to a time-based trigger, such as at periodic intervals, as measured by an external controller or as measured by the bio-chemotronic insert itself. Furthermore, the switching from anon-functionalized state to a functionalized state may occur over only a portion of a bio-chemotronic insert. In some examples, only active agents at certain locations in the bio-chemotronic insert are functionalized for delivery, whereas other active agents in the bio-chemotronic insert are to remaining non-functionalized. In this way, the active agents may be addressable using the integrated controller.

To facilitate operation of the integrated controller, the bio-chemotronic insert may be patterned in logical ways. For example, the controller of the bio-chemotronic insert may be formed having addressable electrical leads. These leads may be part of an actuator layer, and they may connect the controller to each of the active agents of an actuator insert and to each of the sensors of a sensor insert. The resulting individualized control, allows the same bio-chemotronic insert to be used for many different protocols, since the many different combinations of active agents and sensors may be deployed, and in different orders of arrangement.

Another feature of example bio-chemotronic insert systems is the ability to measure and assess sensed response data and functionalize a second active agent in response to the sensed response data. This type of bio-chemotronic insert is termed a progressive bio-chemotronic insert. For example, a bio-chemotronic insert may be configured to release a first active agent stored in an actuator layer upon receipt of an activation signal or upon some other triggering signal. The bio-chemotronic insert may then sense response data from the target. If the integrated controller determines that the response data is within a predetermined range, then the integrated controller may instruct the bio-chemotronic insert to release a second active agent. Indeed, the integrated controller could be configured to release any of a plurality of second active agents each in response to a different range of response data values. Such a bio-chemotronic insert configuration may be used, for example, in a dosage assay bio-chemotronic insert, where a first dosage-level active agent is provided to a target, e.g., a low dosage. Depending on the sensed response of the target, the active agent is administered again, but at a different dosage level. In this way, a single bio-chemotronic insert may be used to incrementally increase dosage delivered to a target. It is noted that while the integrated controller is described as determining which subsequent dosage-level active agent to apply, in other examples, the response data may be communicated to an external controller, such as a network server, which then determines which subsequent dosage-level active agent should be applied, and that information may be communicated back to the bio-chemotronic insert for implementation. Further still, it is noted that the subsequent active agent need not be the same active agent at a different dosage level. Instead, the bio-chemotronic insert may store any number of different functionalizable active agents that may be used as the initial active agent or the subsequent active agent.

Another example implementation of a progressive bio-chemotronic insert is one that releases subsequent active agents by progressively changing the location of the subsequent active agents. Such a bio-chemotronic insert may be used to isolate the location of a targeted pathology, biological process, etc. in a target.

Figure 32:
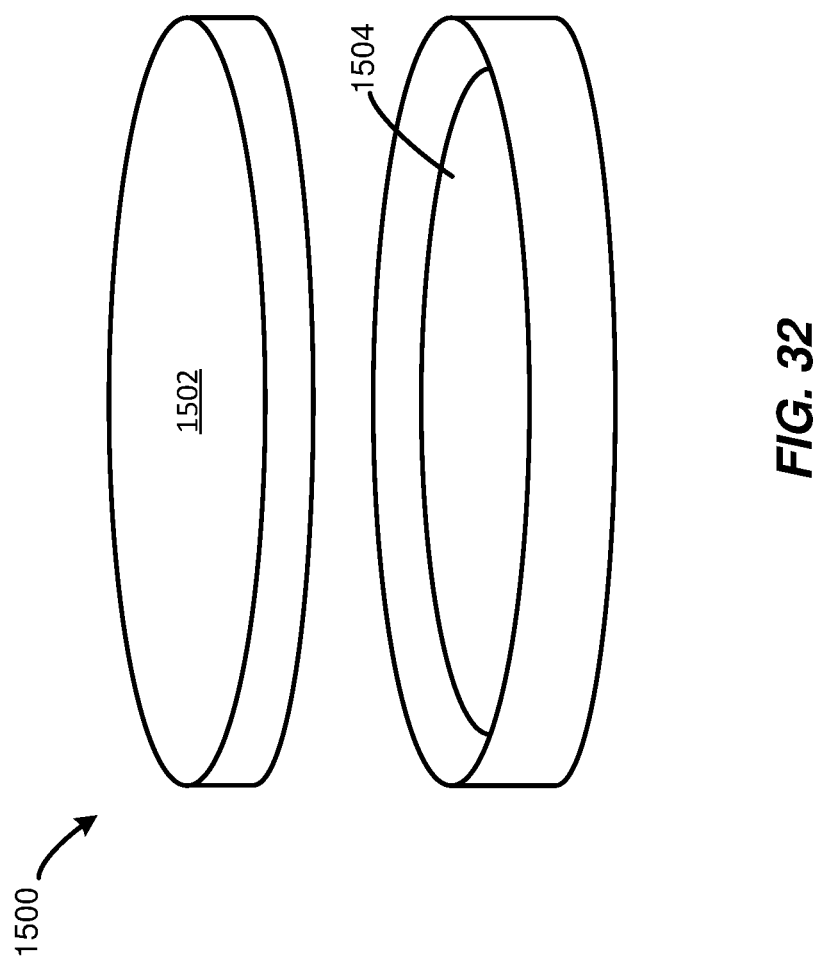
FIG. 32 illustrates another example bio-chemotronic insert in the form of an assay plate, in accordance with an example.

FIG. 32 illustrates another example bio-chemotronic insert 1500 in the form of an assay plate. A cover or insert 1502 operates as an actuator layer and may include activatable agents, such as API's of interest than can be used to affect different sample regions on an assay plate 1504 or sample substrate. Analogous structures may be implemented on the assay plate.

Figure 13A:
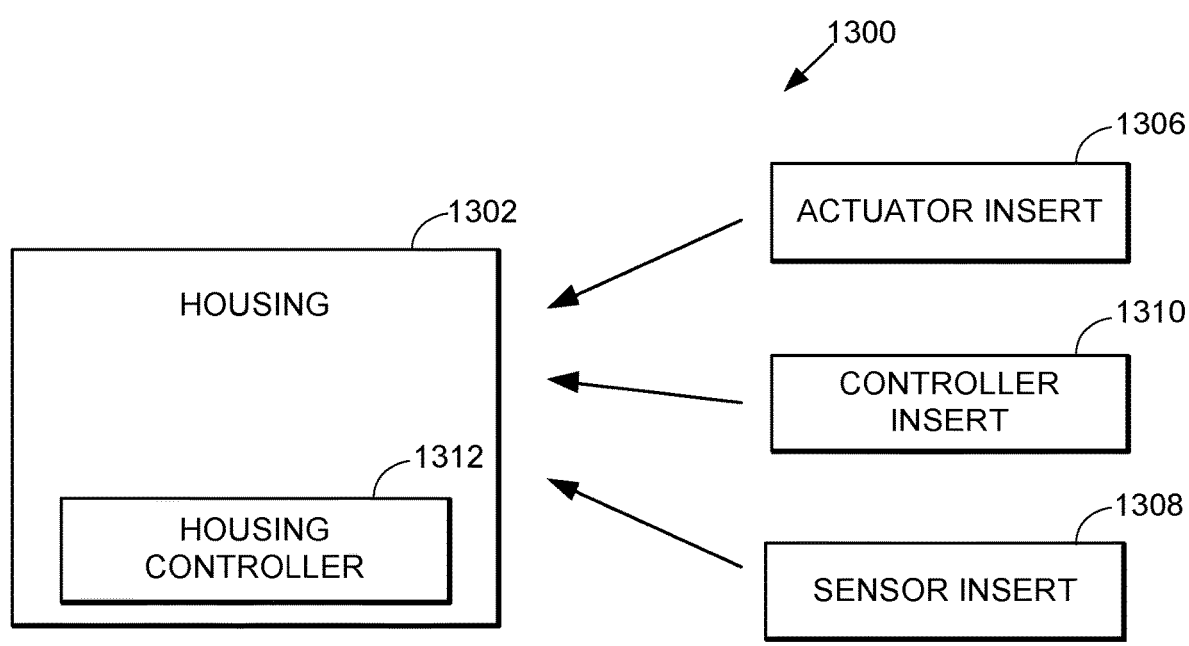
FIG. 13A illustrates a block diagram of a bio-chemotronic insert component system, in accordance with an example.
Figure 13B:
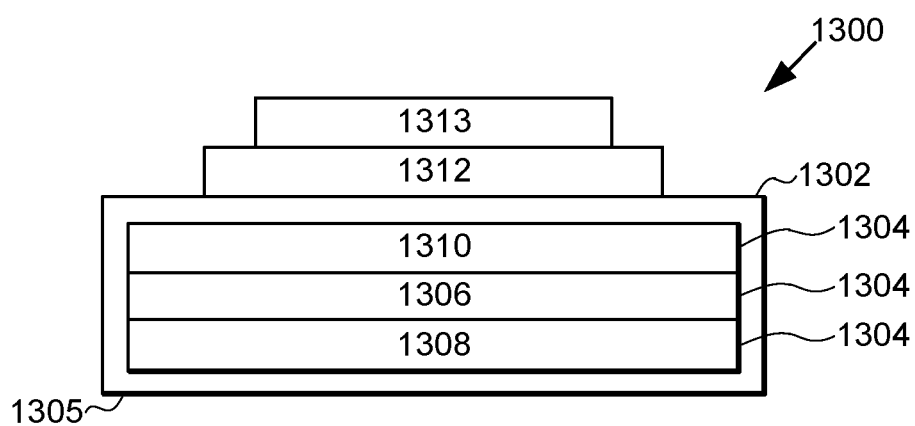
FIG. 13B illustrates a structure of the component system of FIG. 13A, in accordance with an example.
Figure 13C:
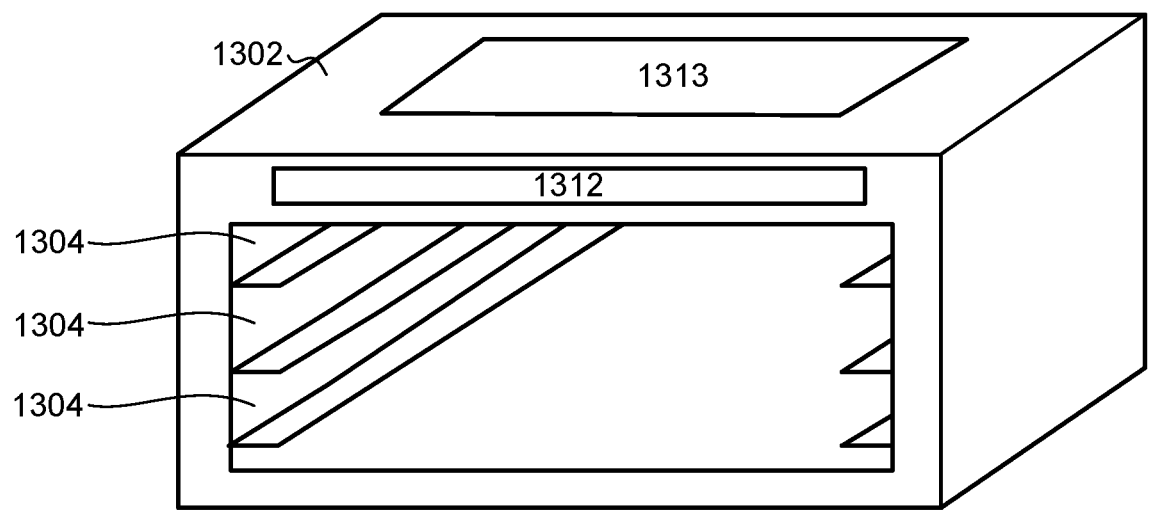
FIG. 13C illustrates an example housing of the component system of FIG. 13A, in accordance with an example.

The bio-chemotronic inserts may be implemented in integrated insert structures, having two or more of the actuator, sensor, control, and interface layers, integrally formed. Yet, in other examples, each of the different layers may be individually formed and provided as a separate insert into an existing architecture. FIGS. 13A-13D illustrate a bio-chemotronic insert component system 1300. FIG. 13A illustrates a block diagram of a system, and FIGS. 13B and 13C illustrate an example implementation thereof. The system 1300 includes a housing 1302 having different receptacles 1304 each configured to receive an insert. The receptacles 1304 may be uniform in shape or receive a standardized insert size. In other examples, one or more of the receptacles 1304 may be configured to receive a particularly sized insert, e.g., a receptacle configured to receive an actuator insert of a first size and a control layer insert of a second size. In the example, the housing 1302 has a permeable layer that operates as a target interface surface 1305 for passing active agents from the system 1300 to a target.

The system 1300 is formed of a separate actuator layer insert 1306, separate sensor layer insert 1308, and separate control layer insert 1310. Each of these inserts is positioned in a different receptacle 1304. The control layer insert 1310 may be positioned, by way of example, in an upper receptacle 1304 and electronically coupled to external circuitry 1312 of the housing 1302 (external to the control layer 1310), circuitry that may include a processor, a memory, a wireless transceiver, an input/output controller, and housing power source. In some such examples, the housing 1302 provides power to the control layer insert 1310 and manages communication with an external controller, such as network server, where, as described elsewhere that communication may include receiving protocol instructions and sending response data for analysis at the server.

The system 1300 may further include a display 1313 for providing instructions to a user or other information, such as protocol information, active agent information, sensed response data information, operation mode information, etc.

Figure 13D:
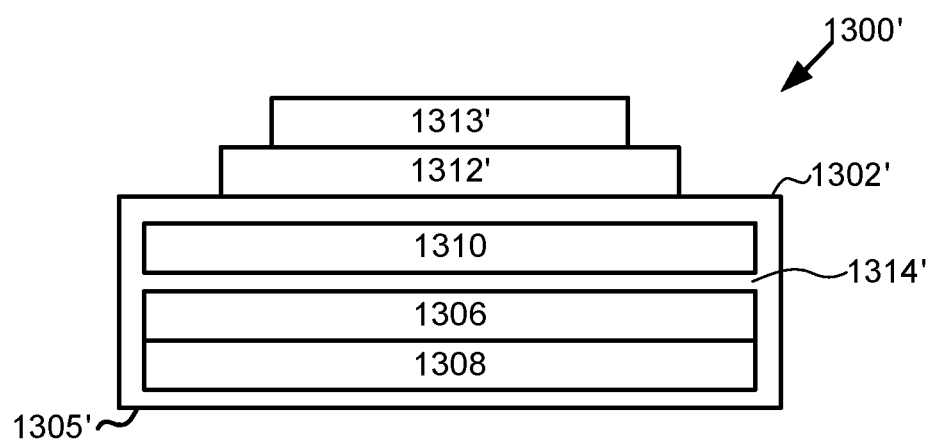
FIG. 13D is an illustration of another example of a structure of the component system of FIG. 13A, in accordance with an example.

Optionally, as shown in the system 1300' of FIG. 13D, the system 1300' may further include an actuator 1314' as part of the housing 1302'. Instead of the control layer insert 1310 functionalizing active agents in the layer 1306 through direct contact, the control layer insert 1310 may be communicatively coupled to the actuator 1314' which then switches the protocol-specified agents from the non-functionalized state to functionalized state. In this way, a bio-chemotronic system may be configured in which the same inserts may be used with different types of housing modules having different actuator mechanisms, including but not limited to electrical resistor elements that will heat up from electrification, thermoelectric elements that can pump heat locally against thermal gradients, thermal heaters that locally vaporize a substance and thereby generate pressure, piezoelectric elements, electroactuated polymers that bend or swell in response to applied electric field, dielectric elastomer actuators, MEMS-based actuators, photostrictive polymer actuators, etc.

Figures 14A, 14B, 14C:
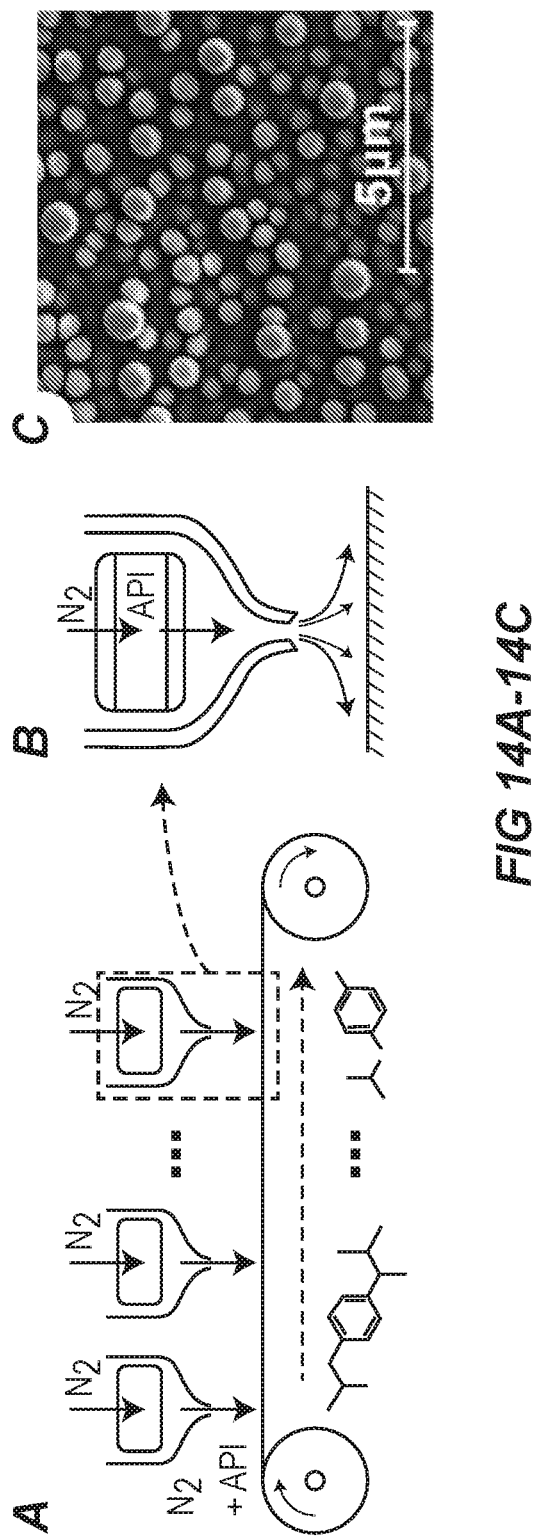
FIGS. 14A-14C illustrate an example process of using organic vapor jet printing (OVJP) techniques to form any of the insert layers of a bio-chemotronic insert, in accordance with an example.
Figures 15A, 15B, 15C, 15D:
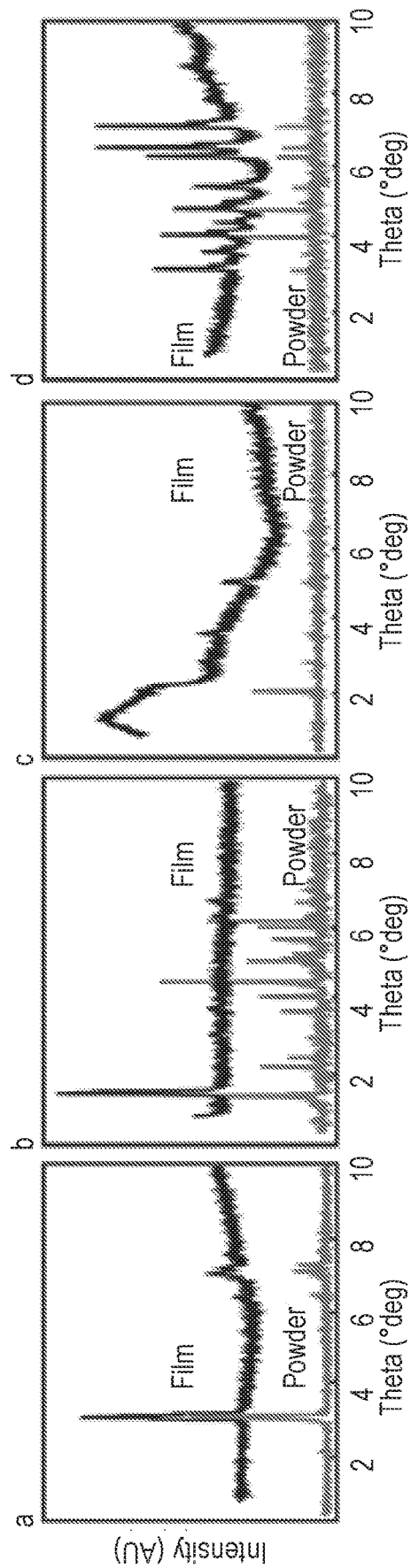
FIGS. 15A-15D are plots of surface X-ray diffraction measurements of thin film layers obtained using specular diffraction, in accordance with an example. (a) Caffeine, (b) Tamoxifen, (c) BAY 11-7082, (d) Paracetamol.

As described herein above, inserts as described herein may be fabricated using, for example, organic vapor jet printing (OVJP) [Shtein et al., Adv. Mater. 16: 1615-1620 (2004), incorporated by reference herein in its entirety]. The OVJP process proceeds by thermally evaporating a substance into a stream of inert carrier gas (e.g., nitrogen), followed by jetting onto a substrate, where the substance forms a film (FIGS. 14A, B). FIG. 14B demonstrates the OVJP working principle. The organic material (e.g., a crystalline powder) is heated, while carrier gas flows over or through it at a predetermined rate. The mixture of evaporated material and carrier gas is jetted onto the cooled substrate, often with a linear velocity exceeding 100 m/sec, enabling a high local deposition rate of up to tens or hundreds of nanometers per second. The process is controlled via several parameters [Biswas et al., Annu. Rev. Chem. Biomol. Eng. 4: 289-317 (2013)], which regulate the dynamics of the gas jet, whose velocity and concentration distributions determine the deposition rate, the deposit shape, as well as the resulting film morphology. In previous publications [Shalev et al., Nature Communications 5: 5204 (2014); Shtein et al., Adv. Mater. 16: 1615-1620 (2004); Sun et al., Appl. Phys. Lett. 86: 103 (2005)] it was demonstrated how the OVJP technique provides morphological control and generates thin (<500 nm) and thick (>500 nm) and large area or localized deposits, while also enabling additive patterning with high material utilization efficiency (>70%). In some cases, when film thickness exceeds 200 nm, the films evolve into unique 3-dimentional nano- and microstructures [Shalev et al., Nature Communications 5: 5204 (2014)]. An example of such a microstructure is shown in FIG. 14C, where a film of fluorescein has evolved "nanolobes" of up to approximately 500 nm diameter. This process occurs due to a combination of forces acting on the film surface during deposition: material condensation, surface diffusion, thermal stresses occurring within a film and molecular structure. The effect of source temperature and deposition duration on size and shape of the structures has been previously demonstrated [Biswas et al., Annu. Rev. Chem. Biomol. Eng. 4: 289-317 (2013); Shalev et al., Nature Communications 5: 5204 (2014)] and a predictive model of the film morphology evolution was developed. Unlike other vapor-based deposition techniques (VTE, chemical vapor deposition, atomic layer deposition and others), OVJP can be performed at atmospheric pressure and in some cases in ambient atmosphere [Biswas et al., Appl. Phys. Lett. 96: 263301-1-3 (2010); Biswas et al., Adv. Funct. Mater. 24, 07-3916 (2014)]. These characteristics, and the fact that the OVJP apparatus itself is conceptually very simple, suggest that OVJP is a perfect candidate for the multiple uses outlined herein.

Additional disclosure around the general concept of insert fabrication is found in PCT/US2016/036009, incorporated by reference herein in its entirety.

EXAMPLES

Example 1

The example describes how films of small molecular medicines (also termed active agents herein) can be made controllably by OVJP, obtaining simultaneously crystalline deposits and enhanced dissolution kinetics.

Methods

Film Fabrication

Caffeine (C0750) >99% was purchased from Sigma Aldrich. Tamoxifen (ICN15673883) >99.24% and paracetamol (5074863) >99.5% were purchased from Fisher Scientific. BAY 11-7082 (19542-67-7) >98% and ibuprofen (401003) >99% were purchased from EMD Millipore, fluorescein (32615) >99.8% was purchased from Fluka; all were used as received. Borosilicate glass slides, 12 mm diameter and 0.2 mm thick, were used as substrates for film deposition. Substrates were cleaned by ultrasonication in detergent solution and deionized water, followed by acetone and isopropanol rinses, for 10 minutes each. Substrates were then placed in boiling isopropanol for 5 minutes and dried in pure nitrogen gas prior to film deposition.

OVJP Process Parameters

OVJP nozzles used in this study were made from quartz tubes having 12.5 mm outer diameter and a nozzle tip of 500 μm internal diameter, with an approximately 15 degree inside wall taper from the nozzle axis. The inert carrier gas was 99.99% pure nitrogen.

The nozzles were cleaned with acetone and isopropanol solvents, dried and wrapped with 36" gauge heavy insulated tape heater (Omega Engineering, Inc.) with a power density of 8.6 W·in$^{-2}$. The heating tape leads were connected to a temperature controller (Digi-Sense Benchtop temperature controller, Cole Palmer Instruments Co.), and a 1/16 inch diameter K type thermocouple was used to monitor and maintain the temperature of the source. The source consisted of approximately 0.15 g of powder embedded in a porous SiC ceramic foam of 100 DPI and placed in the heated source section of the tube. The gas flow rates were maintained using mass flow controllers (C100 MFC, Sierra Instruments).

The process parameters that were kept constant are: nozzle-substrate separation distance (1.5 mm), substrate temperature (20° C.). The process was performed in glove box purged with 99.99% pure nitrogen gas. Detailed processing conditions are given in Table 1.

Deposits were formed by rastering the nozzle over the substrate to form adjacent, overlapping lines at 0.2 mm center-to-center spacing, allowing for homogeneous thickness of deposit for a nozzle of 0.5 mm inner diameter positioned 1.5 mm from substrate surface. Fluorescein films on microneedles were deposited through a flexible mask. The same process can be performed without a mask when using nozzle with appropriate printing resolution.

TABLE 1

OVJP processing conditions for materials used in the study. Source temperature was determined via thermogravimetry and tuned to obtain local deposition rate of approximately 0.5 μg/min

| | Process parameter | | | |
|---|---|---|---|---|
| Material | Carrier gas type | Carrier gas rate (sccm) | Source temperature (° C.) | Substrate temperature (° C.) |
| Fluorescein | Nitrogen | 200 | 300 | 20 |
| Caffeine | Nitrogen | 100 | 130 | 20 |
| Tamoxifen | Nitrogen | 100 | 115 | 20 |
| BAY 11-7082 | Nitrogen | 100 | 90 | 20 |
| Paracetamol | Nitrogen | 100 | 190 | 20 |
| Ibuprofen | Nitrogen | 150 | 75 | 20 |

X-RAY Measurements

Surface X-ray diffraction measurements of the films were performed at Sector 13-BM-C at the Advanced Photon Source, Argonne National Laboratory using a Newport 6-circle kappa diffractometer. FIGS. 15A-15D scans were obtained by specular diffraction (2-theta scan) in which the incident angle was fixed at grazing incidence and the detector scanned the scattered 15 keV X-ray beam. This was done to increase the sampling volume because the films were polycrystalline. The diffracted intensity was collected using a Dectris Pilatus 100K pixel array detector. All measurements were performed in a helium rich environment to prevent rapid degradation of the organic films. Diffraction measurements of powders were performed with Rigaku rotating anode XRD using monochromatic Cu-K-alpha x-ray source. Differences in peak intensities between the powder and film measurements are due to variation in the setups used. The broad feature in FIG. 15C below 1.8° degree is a substrate artifact that could not be eliminated due to the very low angle nature of the measurement.

Microscopy

An FEI Nova 200 Nanolab scanning electron microscope with accelerating voltage of 5-10 kV and current 0.1-0.5 nA was used to obtain the surface morphology images. Optical microscopy analysis was performed with Zeiss microscope (bright field, top-illumination).

Thermogravimetry of Pharmaceutical Substances

To determine evaporation temperature of the powders, and subsequently source temperature in the system, thermogravimetric analysis (TGA) was used. All measurements were performed using a TA Instruments Thermogravimetric Analyzer Q500 at 0.01% accuracy, with nitrogen sample purge flow rate 60 ml/min and balance purge flow rate of 40 ml/min. Heating rate was 5° C./min.

UV-VIS Measurements

Drug dissolution was monitored by in-situ UV-VIS Ocean Optics USB+2000 spectrometer with T300-UV-VIS transmission dip probe, with a 10 mm optical path. Solution absorbance was recorded with frequency of 2-60 sec$^{-1}$ for duration of 20 min-12 hours (depending on substance dissolution rate—fast dissolution rate was recorded at higher frequencies). $\lambda_{max}$ for absorbance testing was: 490 nm for fluorescein, 224 nm for ibuprophen, 240 nm for tamoxifen.

UPLC

To determine the concentration of analyte, and to screen for degradation or impurities, drug powders and films were dissolved in methanol and run on a Waters Acquity H Class UPLC equipped with a Waters Acquity UPLC C18 column (2.1×100 mm). Drug powders were used as standards in all cases, and were diluted such that film samples fell within the range of standards. For all molecules the mobile phase was pumped at 0.3 mL/min, and consisted of A: ddH$_2$O+0.1% Formic Acid and B: Methanol+0.1% Formic Acid. The detection wavelength was set to 280 nm. Caffeine and Paracetemol were run isocratic at 100% B, while Tamoxifen and BAY had a gradient elution starting at A/B: 75/25, to 25/75 at 0.5 mins, steady through 5 mins, then returned to 75/25.

Dissolution Rate Measurement

For dissolution from film, the glass substrate with printed film was attached to rotating rod with substrate holder. In case of compressed powder pellet, 1.57 mm diameter pellet was compressed at 50±2 psi for approximately 10 seconds into a holder having same size as disk substrate holder. In the case of loose powder, the weighed powder was demonstrated into solution and stirred with blank substrate holder at 100 rpm. The detailed dissolution setup is shown in Supplementary Information. In all cases the same vessel and solution volume of 10 ml was used. Testing temperature was room temperature–20±1° C. Sink conditions were defined as C<5Cs. Except for ibuprofen testing, the rest of experiments met sink conditions requirement.

Solubility Tests

Solubility tests were performed at ambient temperature (20±1° C.). Solutions with excess concentration (at least 100 μg/ml of solid) were shaken at approximately 1,000 rpm for 48 hours, followed by solution filtration with 0.4 μm filter after 24 hrs. Filtered solutions concentrations were then measured using UV-VIS spectrometry, calibrated with known solutions concentrations. Five different concentrations for calibration were used in each test. The concentrations used were as follows: for fluorescein in deionized water—1, 2, 3, 4, 5 μg/ml, ibuprofen in HCl pH 1.2 buffer: 2, 4, 6, 8, 10 μg/ml, tamoxifen in acetate buffer pH 4.9: 1, 2, 4, 6, 10 μg/ml.

Theoretical Modeling

Theoretical predictions were calculated according to Noyes-Whitney theory (Equations 2 and 3). The boundary layer thickness according to Levich theory [Levich et al., Journal of The Electrochemical Society 110.11, 251C-252C (1963)] was estimated to be approximately 40 micrometers. Since boundary layer thickness in the rotating disk setup does not depend on compacted powder diameter, D was extracted for each compound based on compacted powder measurement and used for theoretical prediction of loose powders and printed films in plots for FIG. 16, 17. The boundary layer thickness for powder particles was estimated to be the same as particles average size.

Results

Figures 18A, 18B, 18C, 18D, 18E, 18F, 18G, 18H:
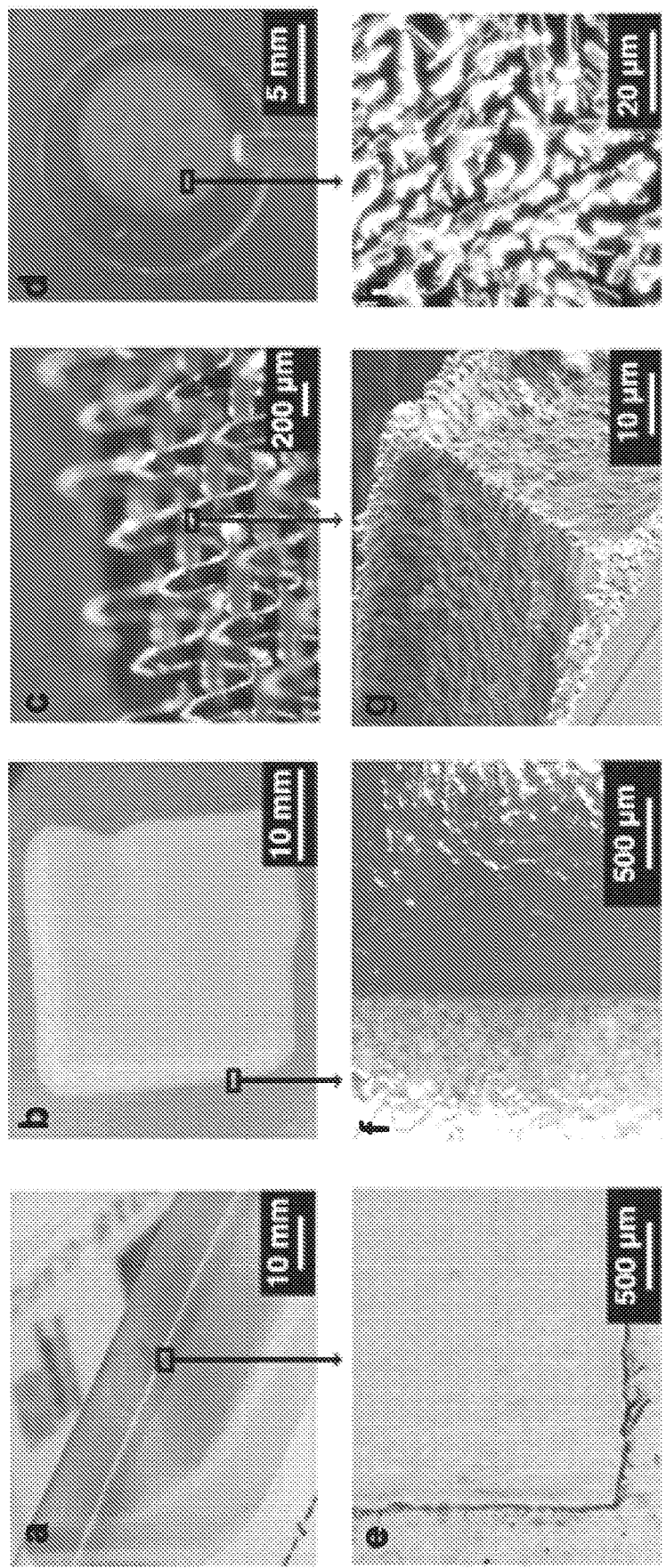
FIGS. 18A-18H are examples of OVJP coatings on different, biomedically important substrates. (a), (e) Fluorescein on 3M™ Tegaderm™, (b), (f) Fluorescein on Listerin®, (c), (g) Fluorescein printed on tips of stainless steel microneedles, (d), (h) Tamoxifen printed with OVJP onto borosilicate glass slides.

Six different drugs (active agents)—caffeine, paracetamol, ibuprofen, tamoxifen, fluorescein and BAY 11-7082 (BAY)—were characterized by thermogravimetric analysis (TGA) [Shalev et al., Organic Electronics 14: 94-99 (2013)] to determine their evaporation temperature and vapor pressure, establishing the conditions for deposition (i.e., flow rate of carrier gas, source temperature, and substrate temperature, as summarized in Table 1). Then, 9 mm diameter circular films were deposited onto borosilicate glass slides (FIG. 18*d*) using identical nozzle geometry in each case, with the deposits characterized using x-ray diffraction, chemical analysis, and high resolution optical and electron microscopies.

Figures 19A, 19B, 19C, 19D, 19E, 19F, 19G, 19H, 19I, 19J, 19K, 19L:
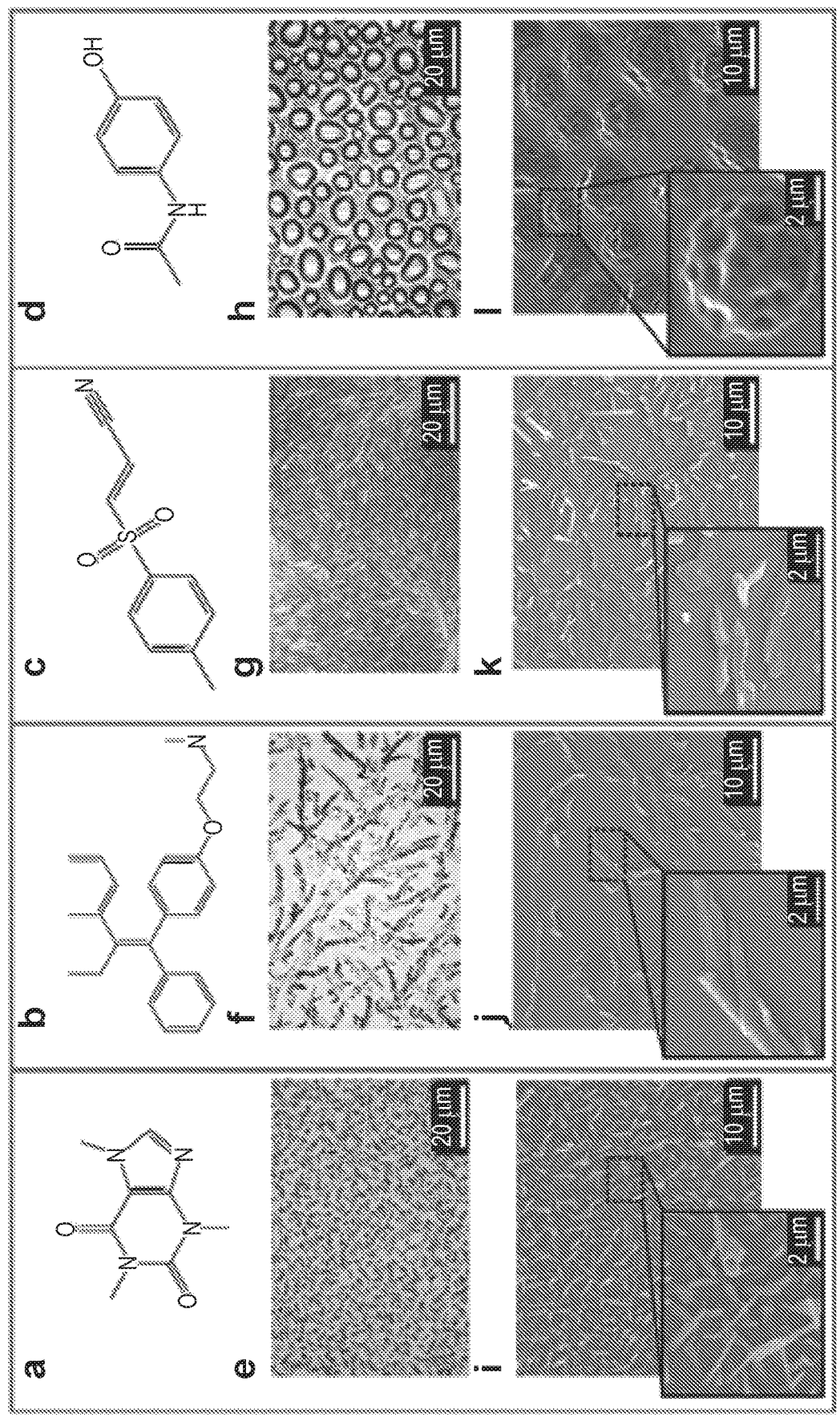
FIGS. 19A-19L illustrate the microstructures of various films. Chemical structure of: (a) Caffeine, (b) Tamoxifen, (c) BAY 11-7082, (d) Paracetamol. Microstructure of OVJP deposited films: (e), (i)—Caffeine, (f), (j)—Tamoxifen, (g), (k)—BAY 11-7082, (h), (l)—Paracetamol.
Figures 20A, 20B, 20C, 20D, 20E, 20F, 20G, 20H:
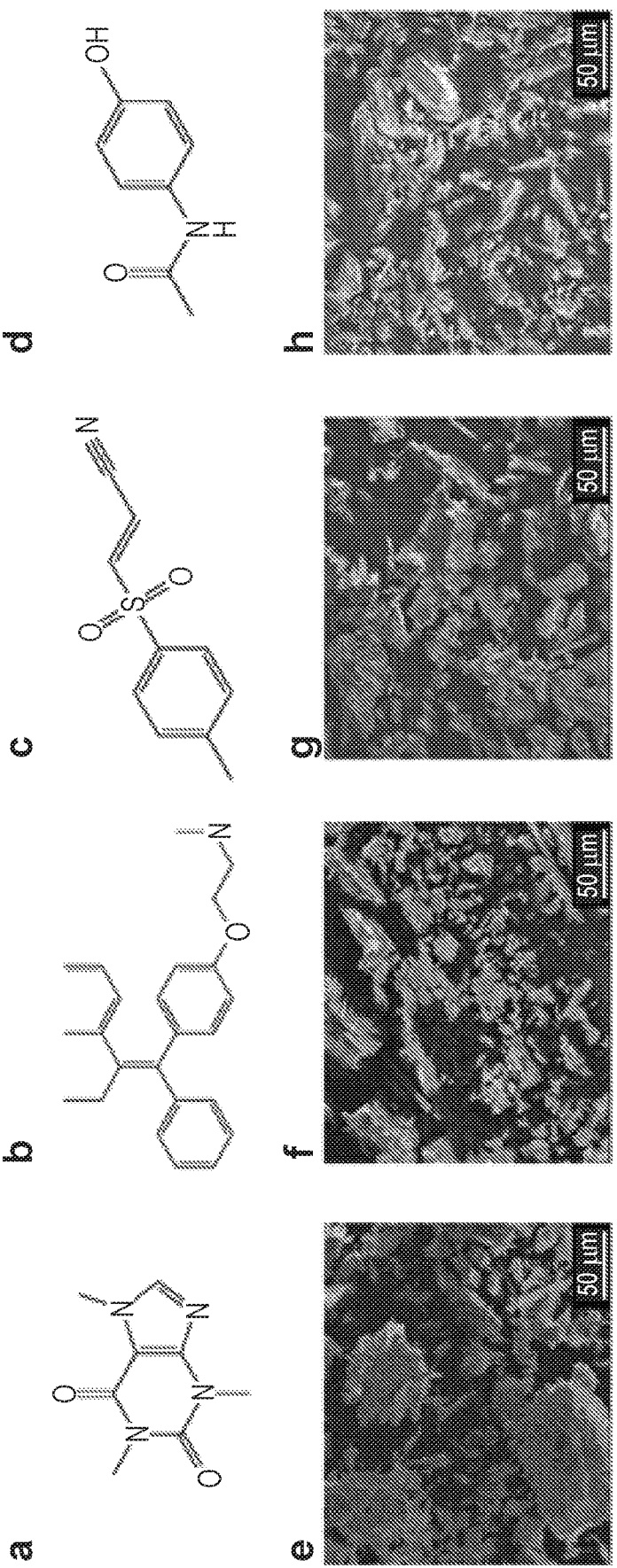
FIGS. 20A-20H show the particle sizes of original coarse powders. (a) Caffeine, (b) Tamoxifen, (c) BAY 11-7082, (d) Paracetamol.
Figures 21A, 21B, 21C, 21D:
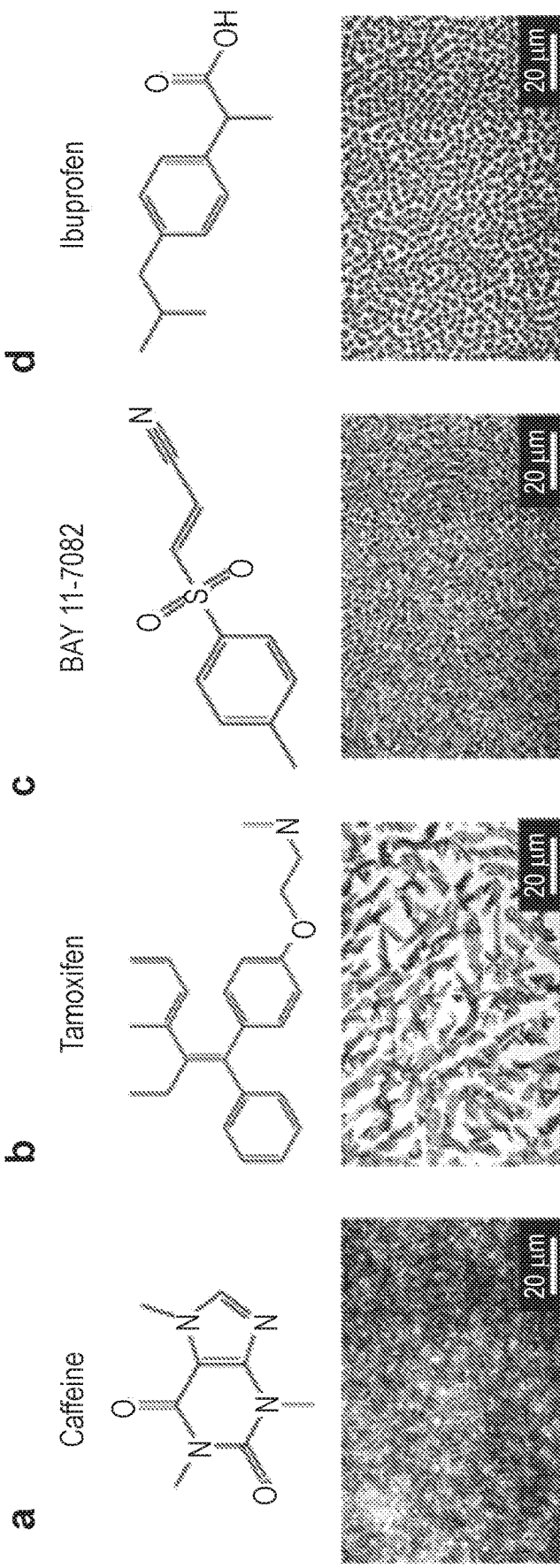
FIGS. 21A-21D show additional optical images of different drug substances printed on silicon (100). The resulting morphology depends on thermophysical properties of drug, substrate material and deposition conditions (Marie, K. K. Flexible continuous manufacturing platforms for solid dispersion formulations. PhD thesis. Rutgers, The State University of New Jersey (2015)). Films were deposited at conditions described in Table 1. (a) Caffeine, (b) Tamoxifen, (c) BAY 11-7082, (d) Paracetamol.
Figures 22A, 22B, 22C, 22D:
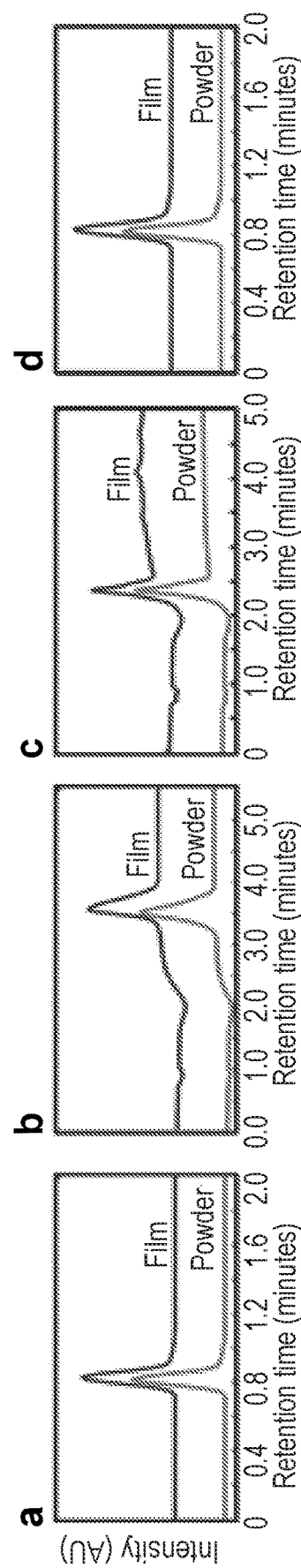
FIGS. 22A-22D show results of Ultra Performance Liquid Chromatography (UPLC) experiments designed to compare the deposited drug films to the original, as-received powder samples. (a) Caffeine, (b) Tamoxifen, (c) BAY 11-7082, (d) Paracetamol.

Examples of the obtained film microstructures are shown in FIG. 19 (where these films represent example actuator inserts, as described herein). All films were evaporated from original coarse powders whose particle sizes ranged approximately between 1-100 μm (FIG. 20). The caffeine coating consisted of needle-like features whose diameter and length were 400±100 nm and 3±1 μm, respectively (FIG. 19A). Tamoxifen films consisted of continuous platelet-like features 800±100 nm and 500±100 nm in height and width, respectively (FIG. 19B). BAY 11-7082 films also consist of discrete platelets-like features 800±100 nm and 500±100 nm in height and width, respectively, and 5±2 μm in length (FIG. 19C). With paracetamol (FIG. 19D) and ibuprofen (FIG. 21), 10 μm diameter, crystallized, interconnected droplets were obtained. The latter morphology was attributed to the fact that paracetamol and ibuprofen were deposited at temperatures of 190° C. and 75° C., respectively, which were 20° C. and 5° C. above their melting point, suggesting that adsorption took place via a transient liquid phase, followed by dewetting and crystallization. In this case the deposit morphology can be tuned by changing the source temperature, carrier gas flow rate, and adjustments to the deposit flux.

Figure 23:
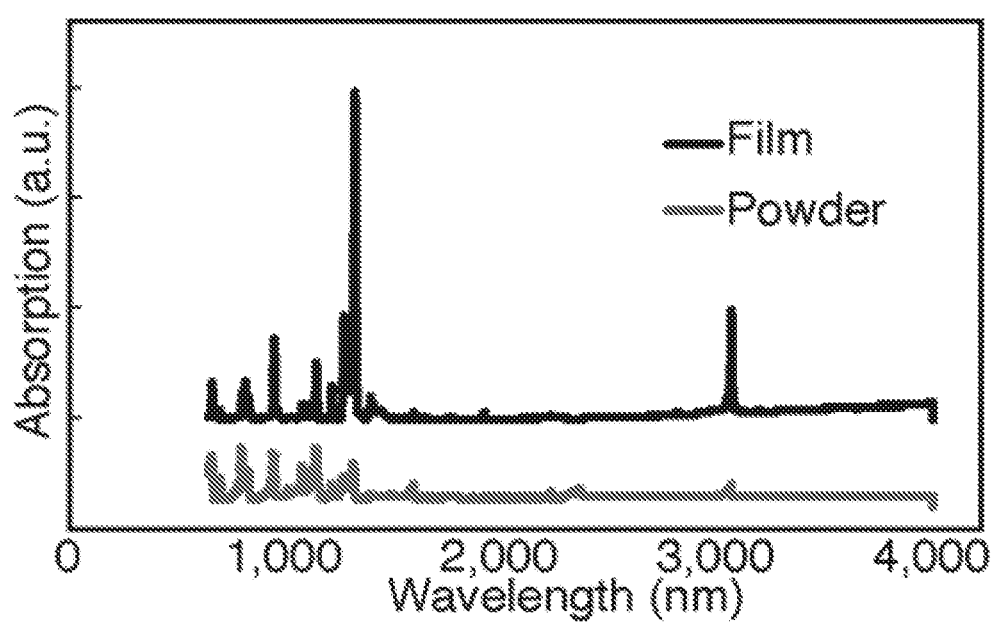
FIG. 23 illustrates that absorption spectra of BAY 11-7082 film and original powder showed similar peaks, assuring that no material degradation occurred due deposition.
Figure 24:
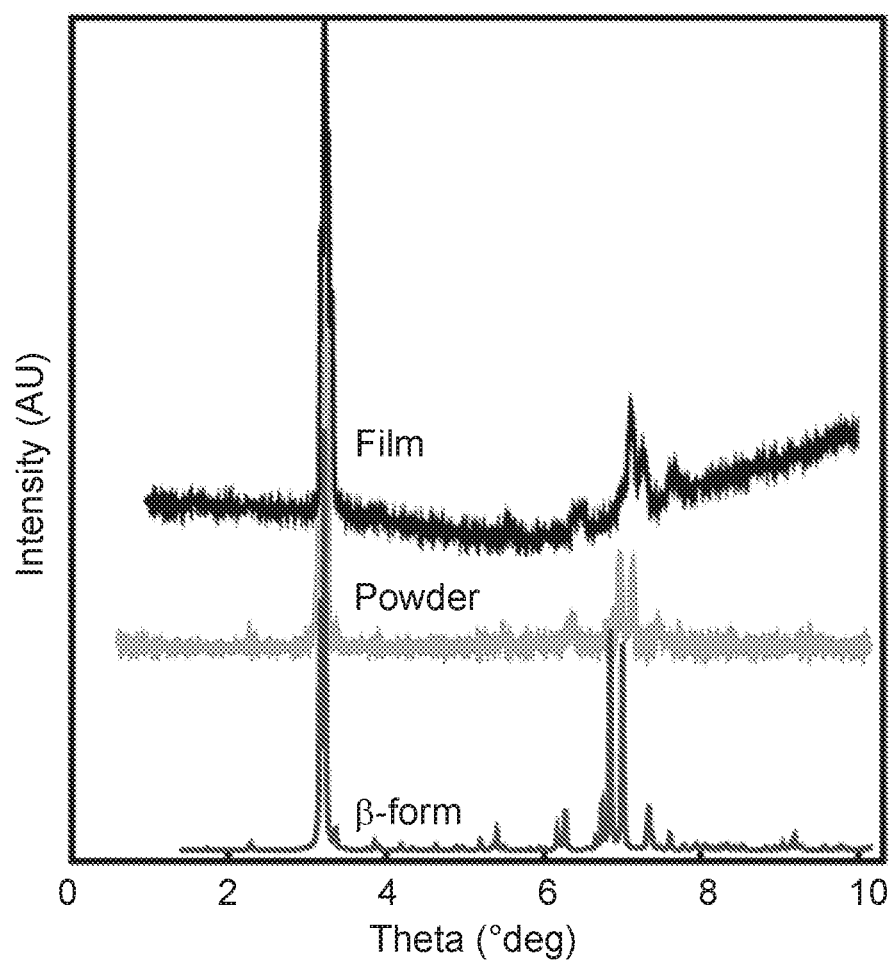
FIG. 24 illustrates a comparison of XRD pattern of caffeine films and original powder to existing phases and shows that both original powder and resulting film are in very good agreement with β-form of caffeine structure.
Figure 25:
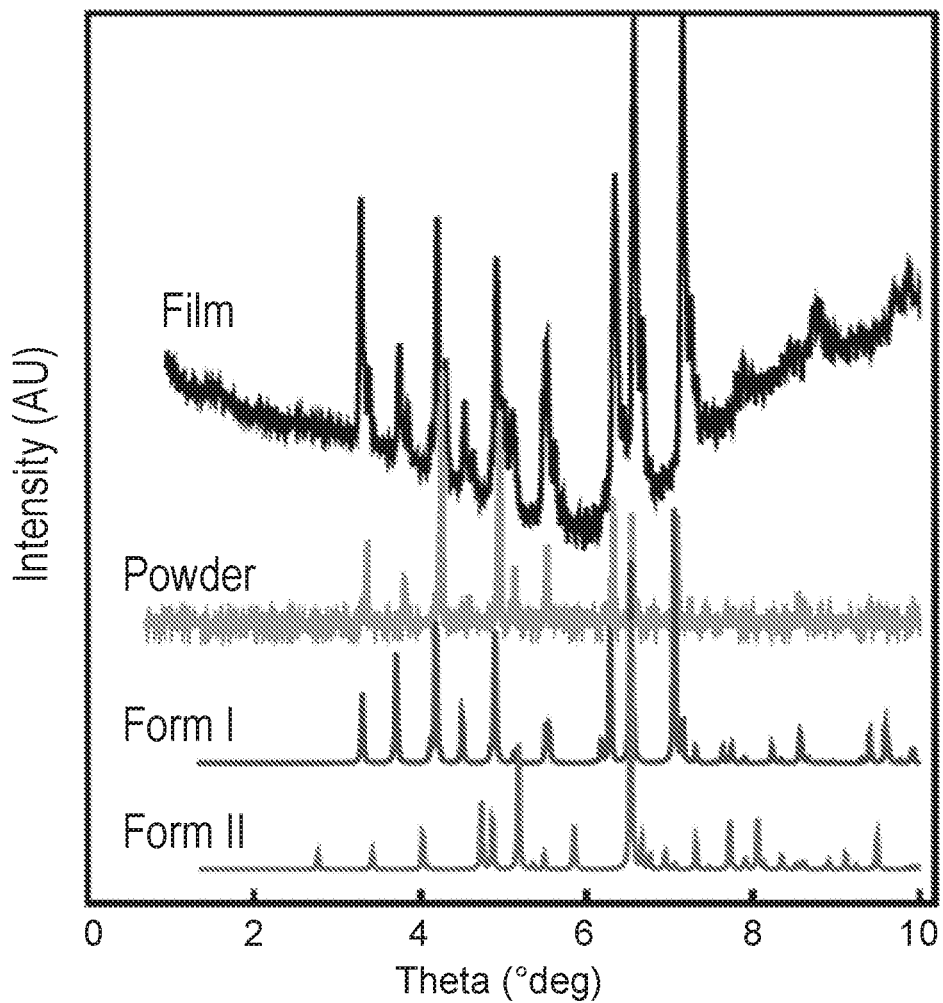
FIG. 25 illustrates that good agreement exists between Form I paracetamol structure, powder and film, with a small amount of Form II admixed.
Figure 26:
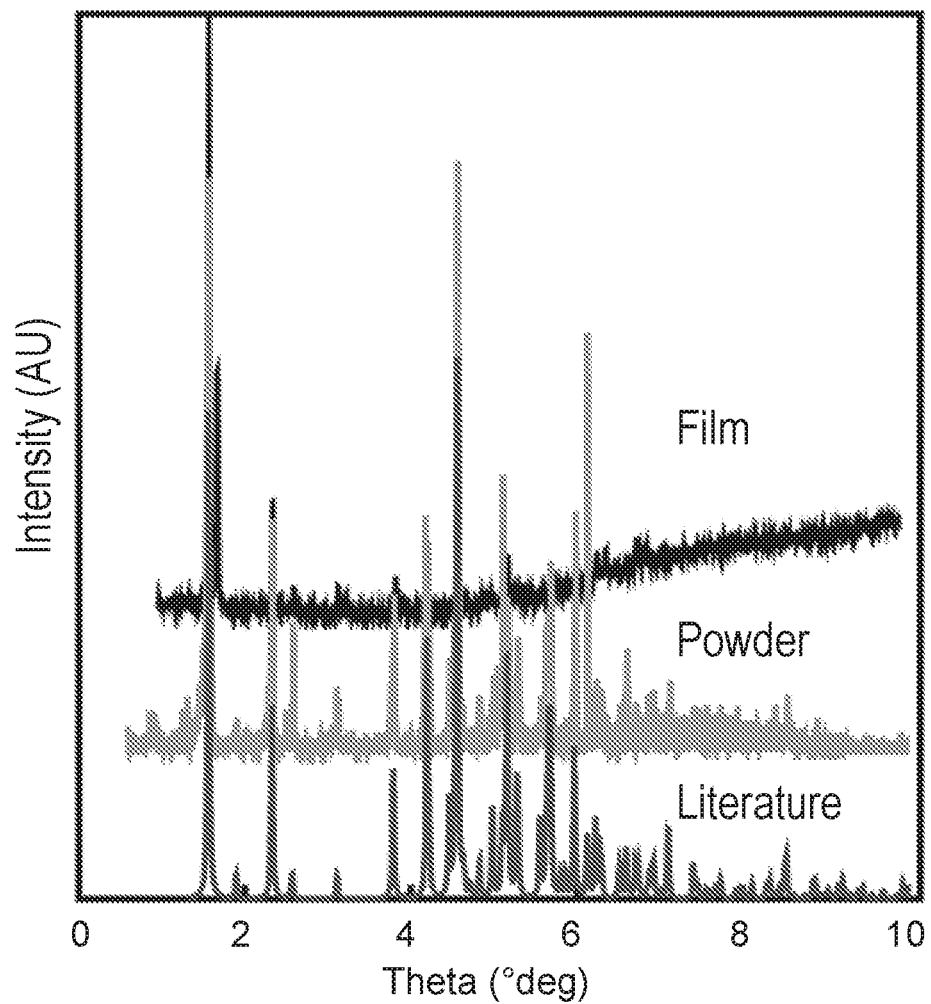
FIG. 26 illustrates plots of a comparison of the crystal structure of the API film for tamoxifen to the structure of the original powder and reference experimental data using synchrotron x-ray diffraction.
Figure 27:
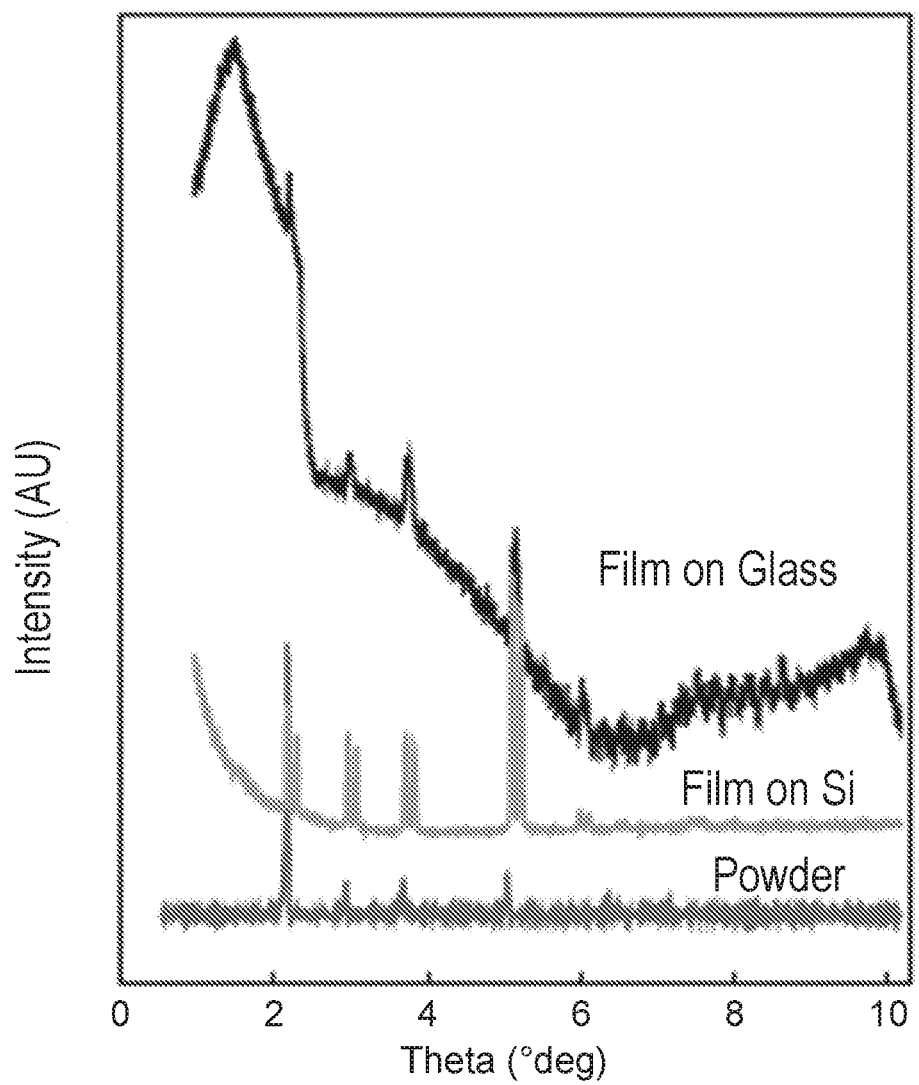
FIG. 27 illustrates a detailed diffraction pattern of BAY 11-7082 original powder and resulting films on glass and silicon substrates. The peak appearing below 1.8° is a measurement artifact, absent for example from the pattern from a film on a silicon substrate, also shown, which lacks this broad artifact.

To test the chemical stability of deposited substances, drug films were dissolved in methanol and analyzed by Ultra Performance Liquid Chromatography (UPLC), for comparison to as-received active pharmaceutical ingredient (API) powder. Similar retention times and peak structures were obtained for deposited films and the original powder samples, (FIG. 22A-D) suggesting that the OVJP process did not alter the chemical structure of the API. Additional tests of BAY 11-7082 film with FTIR (FIG. 23) also revealed no chemical degradation of the material.

Note that for pharmaceutical applications, polymorphism can change drug effectiveness and functionality [Censi et al., Molecules 20: 18759-18776 (2015); Rodriguez-Hornedo et al., Journal of Pharmaceutical Sciences 88(7): 651-660 (1999)]. Hence, the crystal structure of the API films was studied using synchrotron x-ray diffraction and compared to the structure of the original powder and reference experimental data. The diffraction patterns of films were in very good agreement with both bulk powder used in the evaporation source and reference data available on stable materials polymorphs, indicating that OVJP did not change the crystal structure/polymorph composition of the API (FIG. 15A-D, FIG. 24-27). The obtained crystal phase in printed caffeine film was β-form caffeine [Lehmann et al., Chemistry—A European Journal 13, 2908-2911 (2007); Epple et al., Thermochimica Acta 250: 29-39 (1995); Enright et al., Crystal Growth & Design 7: 1406-1410 (2007); Derollez et al., Acta Cryst. B61: 329-334 (2005)], and form I in case of paracetamol [Beyer et al., Journal of the American Chemical Society 123: 5086-5094 (2001); Li et al., Crystal Growth & Design 17: 659-670 (2017); Nelyubina et al., Chem. Commun. 46: 3469-3471 (2010)]. In case of tamoxifen base, crystal structure was similar to powder structure and to the only phase reported in literature [Precigoux et al., Acta Cryst. B35: 3070-3072 (1979)]. The broadening of diffraction peaks in the printed films is attributed to reductions in the average size of the crystallites [B. E. Warren, X-Ray Diffraction (Addison-Wesley Publishing Co., 1969)], compared to that in the original powder. This reduction in crystallite size upon printing occurs due to supersaturation of the API vapor above the substrate, which reduces the critical nucleus size in the formation of new crystallites throughout the deposition process, discussed elsewhere [Shalev et al., Nature Communications 5: 5204 (2014); Biswas et al., Adv. Funct. Mater. 24: 07-3916 (2014)].

The dissolution kinetics of APIs in powder form was compared to that of films printed by OVJP. Accepted pharmacokinetic equations were used to fit the dissolution data, and key differences are highlighted, showing that for drugs printed as films, common limitations of powder dissolution do not exist. This outcome was then used to demonstrate the dosing of poorly soluble drugs in their pure form in a biological system.

To characterize how crystallite size affects the dissolution process, the Noyes-Whitney [Noyes et al., J. Am. Chem. Soc. 19: 930-934 (1897)] equation is often used:

$$\frac{dC(t)}{dt} = \frac{DA(t)}{V\delta(t)}(C_s - C(t)) \quad (1)$$

where C(t) is solute concentration as a function of time, t is time, D is diffusion coefficient in the solvent, A is solute-liquid contact area, V is solvent volume, δ is boundary layer thickness, $C_s$ is the solubility limit in a given solvent. While A can sometimes be measured, boundary layer behavior is often a confounding and poorly controlled variable. OVJP enables the small molecular API to be formed as a continuous film. Although the surface profile may exhibit nanoscale roughness, this fine-scale roughness helps to quickly establish a "virtual surface"—i.e., a saturated boundary layer, which remains at a relatively constant thickness throughout the dissolution process, and therefore opens a new, simplified way of controlling and studying the dissolution process of a drug. Hence, for OVJP-deposited API films, Eq. (1) simplifies to:

$$C(t) = C_s\left(1 - \exp^{\frac{DAt}{V\delta}}\right) \quad (2)$$

For the "sink" condition ($C \ll C_s$), the dissolution rate becomes essentially constant, precisely controlled by the film's projected area.

To characterize powder dissolution kinetics, the Hixson and Crowell model [Hixsonz et al., Industrial and engineering chemistry 23:10: 1160-1168 (1931)] is a simplified solution to Eq. (1):

$$C(t) = \frac{N}{V}\left[Mp_0 - \left(Mp_0^{1/3} - \left(\left(\frac{4\pi}{3\rho^2}\right)^{1/3}\frac{DC_s}{3\delta}\right)^3 t\right)\right] \quad (3)$$

where N is the number of powder particles, $Mp_0$ is particles' initial weight, ρ is solute density. The active contact area in powder dissolution is, in fact, changing during the process, affected by changing particle shape, wettability and tendency to agglomerate—effects that the H-C model does not include [Wang et al., Mol. Pharmaceutics 9: 1052-1066 (2012)]. Note that powder micronization techniques, used to increase the dissolution rate, usually suffer from powder agglomeration, where the effective N/V ratio is reduced, while the effective boundary layer thickness δ often is a strong function of time.

Figures 30A, 30B, 30C:
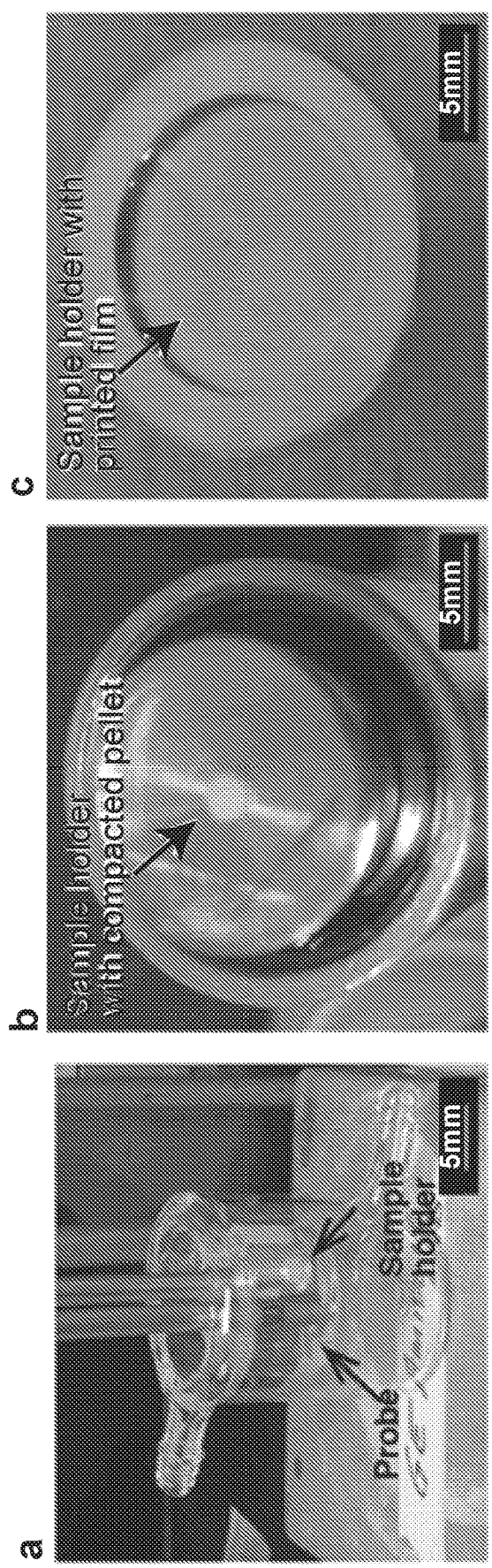
FIGS. 30A-30C illustrate the experimental setup used in dissolution rate studies. (a) Dissolution vessel with optical probe and sample holder. The rod is rotating at 100 rpm speed. (b) Sample holder for miniaturized compressed powder pellet (c) Sample holder for circular substrate with printed film.

The dissolution kinetics of three materials having poor aqueous solubility were studied: fluorescein in deionized water[44], ibuprofen in aqueous hydrochloride (HCl) buffer (pH=1.2) solution[45], and tamoxifen in aqueous acetate buffer solution[46] (pH=4.9). (Caffeine exhibited instantaneous dissolution in the film form, making it impractical to measure its' dissolution kinetics in the film form. BAY 11-7082 was not tested due to low absorbance signal at tested concentrations.) First, the solubility of these compounds in corresponding solvents was measured at 20±1° C. The saturation limit for fluorescein in deionized water was measured to be 10±0.5 µg/ml, for ibuprofen in HCl 22.5±0.5 µg/ml, and for tamoxifen in acetate 23.6±0.5 µg/ml. To measure dissolution kinetics, a rotating disk dissolution apparatus (see FIG. 30 for details) was used with rotational speed of 100 rpm. Concentration was monitored using a UV-VIS spectrometer equipped with a dip probe. The compounds were tested both in powder form (compressed into pellets for rotating disk dissolution) and in film form. The intrinsic dissolution rate (IDR) of the films was compared to the dissolution rate of powder compressed into 1.57 mm diameter pellets of approximate 4 mm thickness [Tseng et al., Dissolution Technologies 21: 24-29 (2014)] (FIG. 30B), while the printed films comprised 9 mm diameter circles on borosilicate glass disks (FIG. 30C). Film weights were in the range 5-80 µg. Identical rotation rod and sample attachments were used (FIG. 30A), assuring that hydrodynamic boundary layer thickness is same for compressed powder and deposited film. Solution volume remained constant in all experiments, 10 ml, and temperature was 20±1° C. In all cases intrinsic dissolution of films was comparable to one of compressed pellets ($3 \cdot 10^{-5} \pm 5 \cdot 10^{-6}$ for fluorescein, $1 \cdot 10^{-3} \pm 3 \cdot 10^{-4}$ for ibuprofen, $6 \cdot 10^{-4} \pm 1 \cdot 10^{-4}$ for tamoxifen, all values in (µg sec$^{-1}$ mm$^{-2}$))). The IDR is defined as:

$$IDR = \frac{(dm/dt)_{max}}{A} \quad (4)$$

where m is the dissolved solute mass, and $(dm/dt)_{max}$ is the maximum slope in the dissolution curve that plots the amount of dissolved material versus time, typically evaluated at the start of dissolution process, where the concentration driving force is highest. IDR is an intrinsic property of a dissolving material, which depends for a given solvent on the material's degree of crystallinity, crystalline and chemical structures. In case of printed films, IDR is essentially unaltered, indicating that material chemical and structural form was not altered either, corroborating XRD and UPLC results.

Figures 16A, 16B, 16C, 16D:
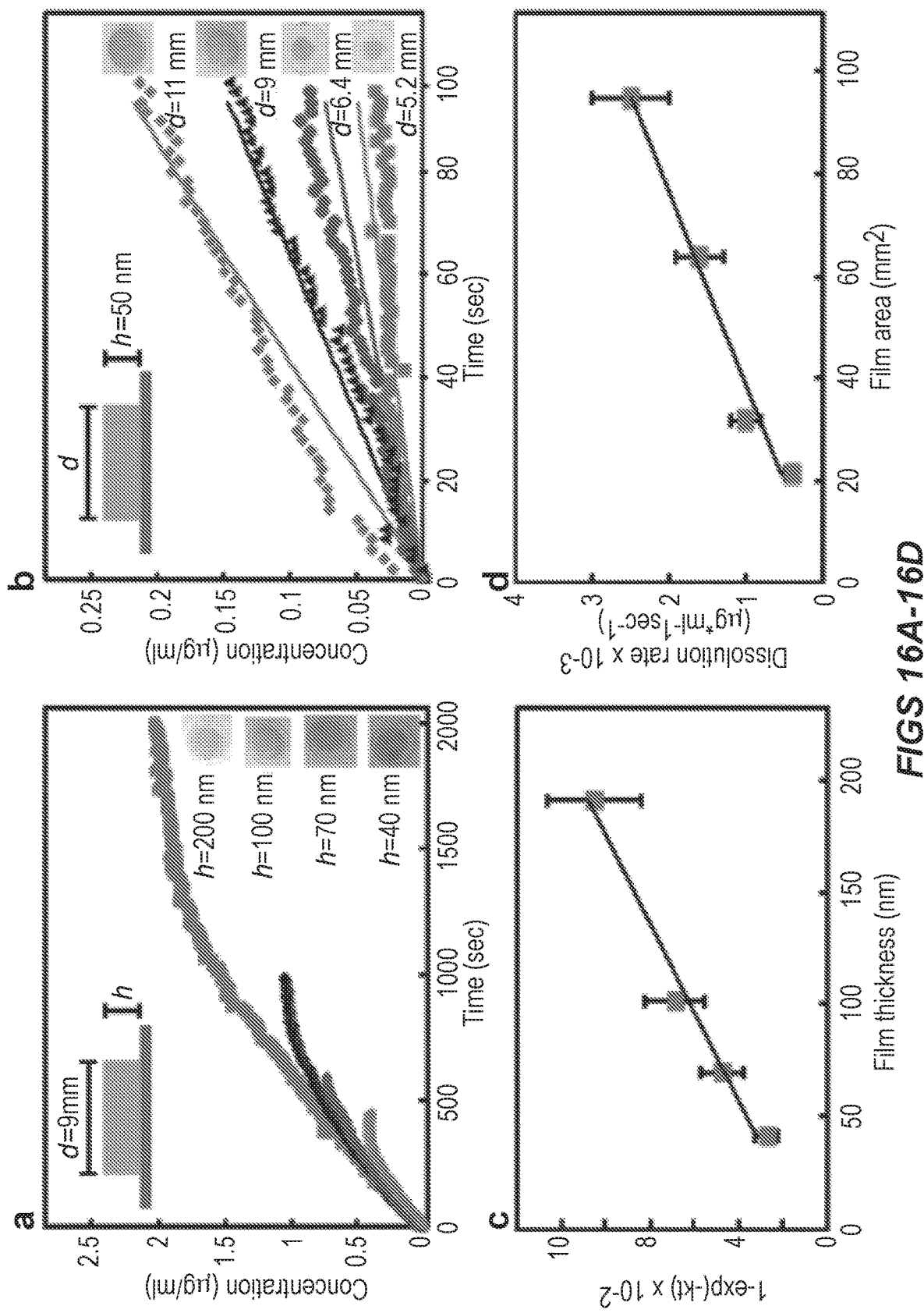
FIGS. 16A-16D illustrate the effect of varying film thickness (a) or film area (b) on dissolution profiles of fluorescein films in deionized water. (c) Dependence of (1-exp(-kt)) (equation 2) on film thickness. Numbers were extracted from data in plot (a). (d) Films dissolution rate vs. film area. The rates were extracted from data in plot (b). Error bars correspond to measurement of at least 3 samples ±STDEV.

FIG. 16 demonstrates how the dissolution rate of films can be controlled via film thickness and deposit area. For example, keeping film area constant, while varying the thickness of the fluorescein film (FIG. 16A), we observe identical IDRs, while the final concentration of fully dissolved sample increases linearly with film thickness; this is confirmed by plotting the right hand side (RHS) of Eq. (2) in FIG. 16C. FIG. 16B shows how concentration varies with deposit area, while keeping the thickness constant. The concentration evolves essentially linearly with time, with the slope proportional to the deposit area, as indicated by a linear fit in FIG. 16D, from which the IDR can be extracted. The dissolution rate scales linearly with film area, as predicted by Eq. (3).

Figures 17A, 17B, 17C:
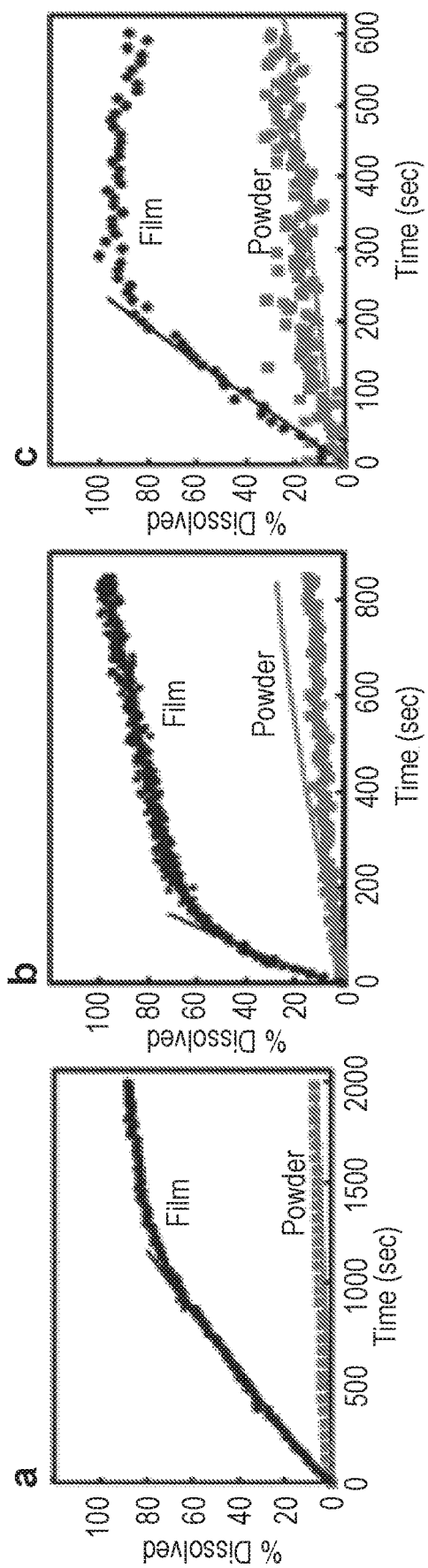
FIGS. 17A-17C show dissolution profiles of films and original powders (dotted line—experimental values. Solid lines—theoretical prediction according to Eq. 2 for film and Eq. 3 for powder): (a) Fluorescein in deionized water—23 μg weight. (b) Ibuprofen in aqueous HCl buffer pH 1.2.-70 μg weight. (c) Tamoxifen acetate buffer pH 4.9-5.5 μg weight.

As-received API powders having the same weight as the films were introduced into 10 ml solutions without any prior treatment, and stirred using a rotation rod with the same shape and diameter as the one used for film dissolution. FIGS. 17A-C demonstrate the dissolution behavior of films versus original loose powders, clearly showing that the initial dissolution rates in films is very rapid and constant up to approximately 80% of the film being dissolved. The dissolution rate is diminished for the remaining material mainly due to reduction in film area (i.e., loss of complete coverage due to material that has dissolved). The initial dissolution rates observed for film-form materials versus loose powders are enhanced ten-fold for fluorescein, thirty-fold for ibuprofen, and ten-fold for tamoxifen. As hypothesized, the initial enhancement in dissolution rate is attributed mainly to the enhancement of surface area of the film, while the IDR or ultimate solubility remain constant. The order of enhancement is in good agreement with the order of enhancement of surface area relative to that of powders. Importantly, film dissolution accurately follows predictions until almost complete dissolution, whereas in the case of powders, the dissolution rate is less predictable due to changes in particle shape and agglomeration [Enright et al., Crystal Growth & Design 7: 1406-1410 (2007)] over time, clearly present for example in the dissolution of ibuprofen powder (FIG. 17B). It is likely that the very high surface area of the vapor deposited films leads to relatively fast establishment of an equilibrium-limited concentration in the boundary layer above the surface, maximizing the driving force for dissolution.

To determine in a controlled manner whether enhanced API dissolution rates translate effectively to the API's action on live cells, two different cancer cell lines (ovarian carcinoma, OVCAR3, and breast carcinoma, MCF7) in growth medium were exposed to tamoxifen films and BAY-11-7082 films printed on glass slides. The cells were plated onto 12-well tissue culture dishes, and allowed to adhere and grow for 24 hours in 2.5 ml of 10% fetal bovine serum-supplemented growth medium. Tamoxifen and BAY-11-7082 films were inverted and placed onto the surface of the growth media, and released from the substrate via gentle, intermittent manual agitation over the course of 1 hour. Slides were removed following this initial period, and live cell counts were determined using trypan blue exclusion using a hemocytometer at 1, 4, 8, 12, 24 and 48 hours following film treatment. At least 3 samples were tested at each time point. Growth inhibition curves were also generated using the following controls: i) Clean glass slides with no deposited drug film as a sham control; ii) 5 µM tamoxifen or 500 nM BAY-11-7082 dissolved in dimethyl sulfoxide (DMSO; conventional drug dose); iii) tamoxifen or BAY powders dissolved directly in sterile supplemented growth medium. In all cases, the amount of the introduced drug was calculated such that the nominal concentration of the treatment was 5 µM (1.8 µg/ml) for tamoxifen (4.5 µg per film) and 500 nM (0.1 µg/ml) for BAY 11-7082 (0.25 µg per film).

Figures 28A, 28B, 28C, 28D:
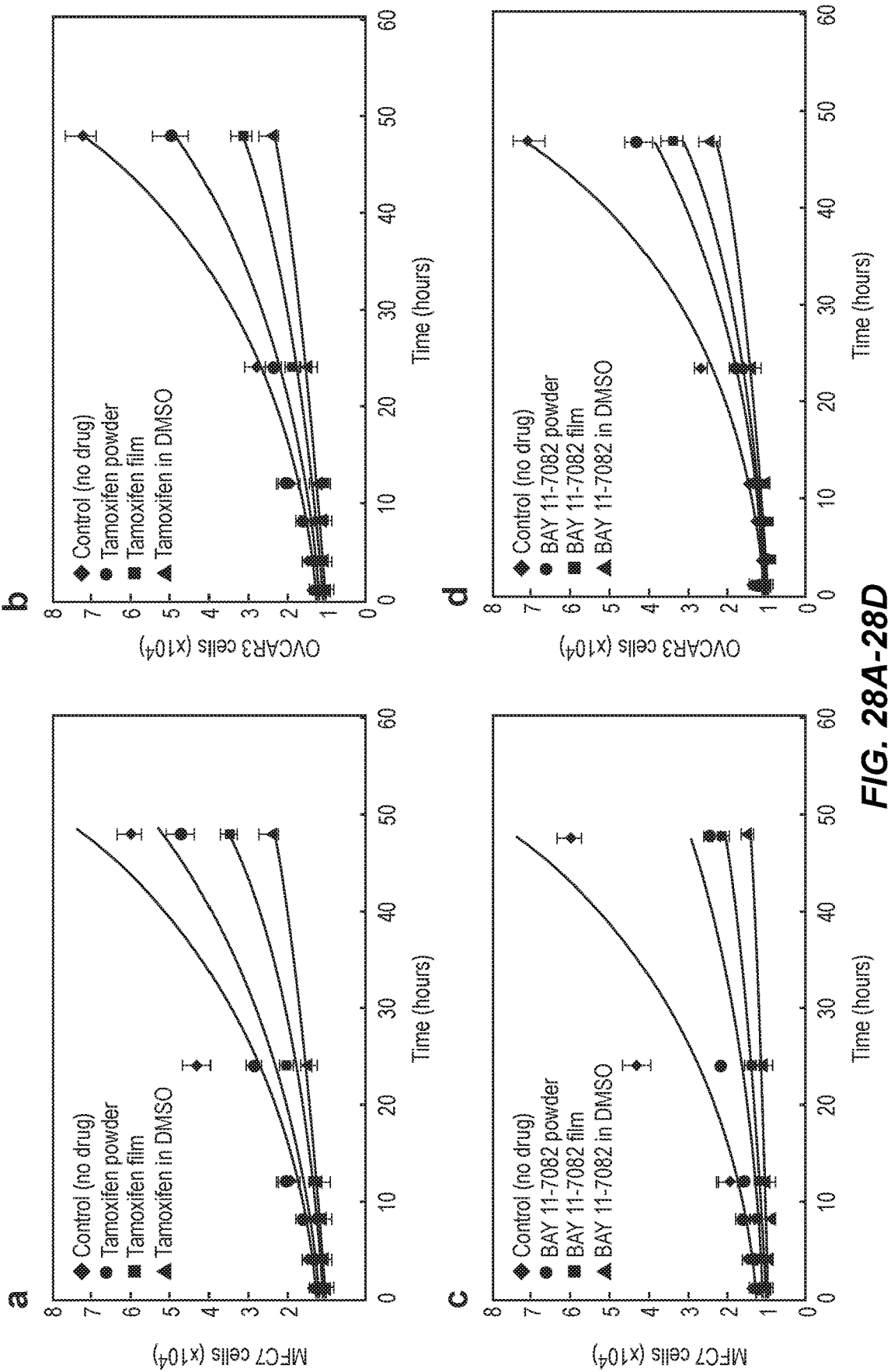
FIGS. 28A-28D illustrate cell growth profiles (solid line—eye guide): (a) MCF7 cells treated tamoxifen, (b) OVCAR3 cells treated with tamoxifen, (c) MCF7 cells treated with BAY 11-7082, (d) OVCAR3 cells treated with BAY 11-7082. All data points in the plots are an average of at least 3 film samples ±STDEV.
Figure 29A:
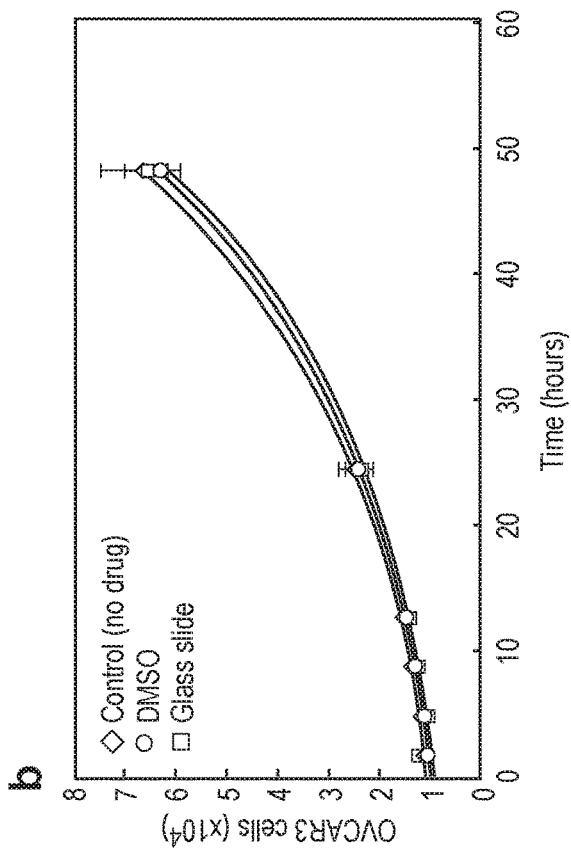
FIGS. 29A and 29B illustrate cancer cell growth curves—cell growth at drug-free conditions. To ensure that glass slide doesn't affect cell growth, three drug-free control studies were performed: medium with just cancer cells, medium with just cancer cells and DMSO, medium with just cancer cells and glass slide. No effect of glass slide on cell growth was observed.
Figure 29B:
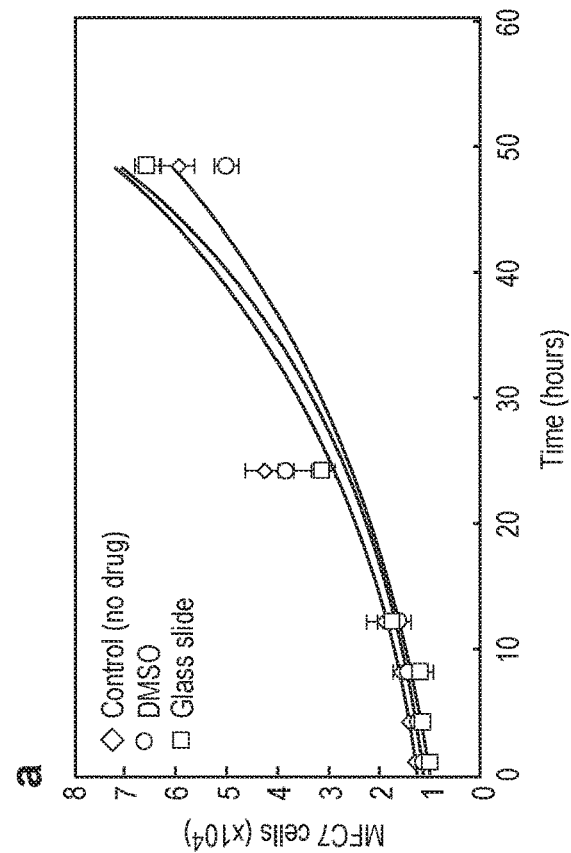

FIG. 28 demonstrates cancer cell count curves treated with the different drug forms. All data points in the plots are an average of at least three film samples. In both cases, cells treated with film-form drug showed significantly reduced viability, comparable to when the drug was pre-dissolved in DMSO. MCF7 cancer cells' viability after 48 hours was 58% for film form and 79% for powder form treatment (FIG. 28a), and OVCAR3 cancer cells' viability after 48 hours was 44% for film form and 68% for powder form treatment (FIG. 28b). BAY-11-7082 films exhibited similar effectiveness as the powdered drug dissolved in growth medium (FIGS. 28C, 28D). Importantly, DMSO alone and neat substrate alone did not show an impact on the cancer cell growth as shown in FIG. 29 The lower effectiveness of powder-form dosing in tamoxifen is attributed to slower dissolution and, hence, smaller effective concentration of the drug relative to that obtained from the films.

The foregoing example demonstrates the solvent-free printing of small molecular pharmaceutical ingredients (i.e., active agents) to obtain high surface area films having nanocrystalline morphology (i.e., actuator inserts). These printed films exhibit substantially enhanced dissolution kinetics compared with their bulk powder form. Drug films printed in this manner (shown here for tamoxifen and BAY-11-7082) exhibit enhanced cancer cell-killing properties in vitro, without having to pre-dissolve them in organic solvents, such as DMSO. While amorphous dispersions have been used to increase the APIs' solubility, their stability remains questionable [Baghel, S., Cathcart, H. & O'Reilly, N. J. Polymeric Amorphous Solid Dispersions: A Review of Amorphization, Crystallization, Stabilization, Solid-State Characterization, and Aqueous Solubilization of Biopharmaceutical Classification System Class II Drugs. Journal of Pharmaceutical Sciences in press, 1-18 (2016)], while the polycrystalline nature of the printed films suggests a promising avenue for breaking the trade-off between stability and dissolution rates.

More generally, the ability to deposit small molecular drugs (i.e., active agents) from their pure form, as films and without the use of solvents as shown here, may be used to form the bio-chemotronic components and devices described herein. Such bio-chemotronic components and devices may be used for drug screening, where accurate dosage, chemical and structural stability, and processing flexibility are needed without hindering drug functionality. As described, these bio-chemotronic components and devices can be used for any number of active agent applications. Advantages of the foregoing disclosure include benefits in: (a) early stage drug discovery—enabling eliminating the need for organic solvents for poorly soluble drugs during screening processes, (b) development of drug delivery vehicles—e.g., films for transdermal drug delivery, directly coated patches, microneedles, encapsulated dissolvable films or implants, and (c) administration of high potency APIs (HPAPIs) with accurate and individualized dosing and nanogram-level accuracy without compromising safety during manufacturing. The technique demonstrated here also enables continuous manufacturing, where films and polymers can be alternately deposited [Sun et al, Appl. Phys. Lett. 86, 103 (2005); Han et al., Scientific reports 6: 24158, 1-10 (2016)] to obtain desired dosage availability, and versatile formulation, eliminating the need for mixing and powder preparation.

As described, these OVJP techniques may be used to form any of the layers and inserts described herein, including the actuator layers, sensor layers, control layers, etc. For the control layers and sensor layers, for example, OVJP techniques may be used to form organic semiconductor and electronic devices, including optoelectronic devices. In addition to those described above, other example OVJP techniques are described in Biswas, Thin-Film Growth and Patterning Techniques for Small Molecular Organic Compounds Used in Optoelectronic Device Applications, Annu. Rev. Chem. Biomol. Eng. 2013. 4:289-317, which is hereby incorporated by reference in its entirety. In any event, the OVJP techniques described herein are able to employ very precise deposition of organic molecules using shadow masking, to enable direct, additive patterning of small molecular organic semiconductors. As described, organic material may be evaporated into a carrier gas, which, upon picking up the vapor, is ejected at high velocity through a collimating nozzle directed at the cooled substrate, and patterned to form the layers and inserts described herein. And as such, OVJP may be used to form any number of components in a thin film layer to form sensor layers and control layers. Example components include organic light-emitting devices, organic thin-film transistors, organic semiconductor lasers, organic photovoltaic cells, and organic photodetectors, and combinations thereof. OVJP fabrication is particularly useful in forming these types of organic components, given that OVJP enables additive patterning of the active layers involved in charge and exciton transport, light absorption or emission, and other important functions in the components forming thin-layer sensors and then-layer control electronics.

Control layers, for example, may be fabricated with organic thin-film transistors configured to control actuating components within the control layer to switch one or more of the active agents from a non-functionalized to a functionalized state. The actuating components could be thermal actuators like electrodes, thermistors, etc. In some examples actuating components could be light based actuators such as organic light-emitting diodes or organic semiconductor lasers, each similarly formed in the control layer. Sensor layers may be formed of organic photodetectors, organic photovoltaic cells, organic bioanalyte sensors, optical sensors, pressure sensors, temperature sensors, organic chemical sensors, organic semiconductor electrical sensors, etc. As such, OVJP can be used to form any of the actuator, sensor, and control layers. One of the advantages of OVJP can be used to form such layers individually, such as when forming these layers as separate insert. In other examples, OVJP is used to form integrated layers, such as those described in above (see, e.g., FIG. 1).

While OVJP techniques are particularly useful, other fabrication techniques may be used. These include organic molecular beam deposition, vacuum thermal evaporation, and organic vapor phase deposition, other molecular jet printing techniques, or combinations thereof.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a central processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A controllable solid film device, the device comprising:
    a solid film layer structure containing (i) an actuator insert having a low molecular weight organic active agent, wherein the low molecular weight organic active agent has a first state in the actuator insert in which the low molecular weight organic active agent is de-functionalized and a second state in which the low molecular weight organic active agent is functionalized for application to a target, and (ii) a sensor insert having a sensor configured to measure response data indicating a response of the target to receiving the applied low molecular weight organic active agent, wherein the actuator insert and the sensor insert are separate from one another and retained in different layers of the solid film layer structure;
    an interface layer positioned for applying the solid film device to the target after changing the low molecular weight organic active agent from the first state to the second state, for providing a barrier between the solid film layer structure and the target, and for releasing the low molecular weight organic active agent through the interface layer to the target; and
    a control layer positioned relative to the solid film layer structure for the changing the low molecular weight organic active agent from the first state to the second state and for communication with the sensor insert to receive the response data.

2. The solid film device of claim 1, wherein the actuator insert comprises at least one additional low molecular weight organic active agent, each of the at least one additional low molecular weight organic active agents having a first state in the actuator insert in which each of the at least one additional low molecular weight organic active agents is de-functionalized and a second state in which each of the at least one additional low molecular weight organic active agents is functionalized for application to the target, and
    wherein the control layer is configured to independently change each of the at least one additional low molecular weight organic active agents from its first state to its second state.

3. The solid film device of claim 2, wherein the low molecular weight organic active agent and the at least one additional low molecular weight organic active agent differ from one another in dosage level.

4. The solid film device of claim 2, wherein the low molecular weight organic active agent and the at least one additional low molecular weight organic active agent differ from one another in chemical composition.

5. The solid film device of claim 4, wherein the actuator insert is configured to co-locate the low molecular weight organic active agent and the at least one additional low molecular weight organic active agent in the actuator insert for application to a same location within the target.

6. The solid film device of claim 2, wherein the low molecular weight organic active agent and the at least one additional low molecular weight organic active agent are each contained in a different sub-layer of the actuator insert.

7. The solid film device of claim 2, wherein the low molecular weight organic active agent and the at least one additional low molecular weight organic active agent are each positioned in a different location in a single layer of the actuator insert.

8. The solid film device of claim 7, wherein the low molecular weight organic active agent and the at least one additional low molecular weight organic active agent are each positioned in the single layer of the actuator insert so that each of the low molecular weight organic active agent and the at least one additional low molecular weight organic active agent are to be applied to a different location on the target.

9. The solid film device of claim 2, wherein the sensor insert comprises at least one additional sensor, wherein each of the at least one additional sensors are configured to measure respective response data indicating a response to a different one of the at least one additional low molecular weight organic active agents.

10. The solid film device of claim 9, wherein the sensor and the at least one additional sensor are positioned within the sensor insert to each measure the respective response data at a different location on the target.

11. The solid film device of claim 2, wherein the control layer is configured to:
    (i) change at least one of the at least one additional low molecular weight organic active agents from its first state to its second state;
    (ii) receive the response data from the sensor insert;
    (iii) based on the response data, identify a subsequent low molecular weight organic active agent from the at least one additional low molecular weight organic active agents; and
    (iv) change the subsequent low molecular weight organic active agents from its first state to its second state.

12. The solid film device of claim 1, wherein the control layer further comprises a wireless transceiver for communicating with an external network-accessible controller.

13. The solid film device of claim 12, wherein the control layer is configured to change the low molecular weight organic active agent from the first state to the second state in response an activation signal received from the external network-accessible controller.

14. The solid film device of claim 12, wherein the control layer is configured to communicate the response data to the external network-accessible controller and wherein the controller layer is configured to receive subsequent instructions from the external network-accessible controller.

15. The solid film device of claim 1, wherein the control layer is configured to change the low molecular weight organic active agent from the first state to the second state in response a time-based trigger.

16. The solid film device of claim 1, wherein the control layer is configured to change the low molecular weight organic active agent from the first state to the second state in an impact event on the solid film device.

17. The solid film device of claim 1, wherein the control layer is configured to change the low molecular weight organic active agent from the first state to the second state in response to an external trigger signal wirelessly communicated to the control layer.

18. The solid film device of claim 1, wherein the low molecular weight organic active agent comprises melatonin, antihistamine, caffeine, ibuprofen, and/or indomethacin.

19. The solid film device of claim 1, wherein the sensor is configured to sense concentration of a bioanalyte in the target in response to the application of the low molecular weight organic active agent.

20. The solid film device of claim 19, wherein the bioanalyte is an allergen or a histamine.

21. The solid film device of claim 1, wherein the control layer is part of the solid film layer structure, and the actuator insert, the sensor insert, and the control layer are sandwiched together.

22. The solid film device of claim 1, wherein the second state in which the low molecular weight organic active agent is functionalized for application to the target is a progressive functionalized state capable of having different characteristics in the second state.

23. The solid film device of claim 1, wherein the sensor of the sensor insert has a first sensor state, wherein the sensor is not active to sense for the response data, and a second sensor state, wherein the sensor is active to sense for the response data, wherein the first sensor state and the second sensor state are switchable through an external control from the control layer.

24. The solid film device of claim 1, wherein the solid film device is an electronically-controllable solid film device and the control layer comprises a processor.

\* \* \* \* \*

UNITED STATES PATENT AND TRADEMARK OFFICE
CERTIFICATE OF CORRECTION

PATENT NO. : 12,208,227 B2
APPLICATION NO. : 16/641505
DATED : January 28, 2025
INVENTOR(S) : Max Shtein et al.

Page 1 of 1

It is certified that error appears in the above-identified patent and that said Letters Patent is hereby corrected as shown below:

In the Claims

At Column 33, Line 1, "response" should be -- response to --.

At Column 33, Line 12, "response" should be -- response to --.

Signed and Sealed this
Twenty-seventh Day of May, 2025

Coke Morgan Stewart
*Acting Director of the United States Patent and Trademark Office*